US008862206B2

(12) United States Patent
Wang et al.

(10) Patent No.: US 8,862,206 B2
(45) Date of Patent: Oct. 14, 2014

(54) EXTENDED INTERIOR METHODS AND SYSTEMS FOR SPECTRAL, OPTICAL, AND PHOTOACOUSTIC IMAGING

(75) Inventors: Ge Wang, Blacksburg, VA (US); Yong Xu, Blacksburg, VA (US); Alexander Cong, Blacksburg, VA (US); Haiou Shen, Blacksburg, VA (US); Wenxiang Cong, Christiansburg, VA (US); Lin Yang, Ithaca, NY (US); Yang Lu, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 986 days.

(21) Appl. No.: 12/945,733

(22) Filed: Nov. 12, 2010

(65) Prior Publication Data

US 2011/0282181 A1 Nov. 17, 2011

Related U.S. Application Data

(60) Provisional application No. 61/260,543, filed on Nov. 12, 2009, provisional application No. 61/260,566, filed on Nov. 12, 2009, provisional application No. 61/289,100, filed on Dec. 22, 2009.

(51) Int. Cl.
*A61B 5/05* (2006.01)
*G01N 23/04* (2006.01)
*G06T 11/00* (2006.01)
*A61B 6/00* (2006.01)
*A61B 6/03* (2006.01)
*A61B 5/00* (2006.01)

(52) U.S. Cl.
CPC .............. *A61B 6/032* (2013.01); *G01N 23/046* (2013.01); *G06T 11/006* (2013.01); *G06T 2211/436* (2013.01); *A61B 5/7232* (2013.01); *A61B 6/4007* (2013.01); *A61B 5/0095* (2013.01); *G06T 2211/424* (2013.01); *G06T 2211/432* (2013.01)
USPC ........... 600/425; 600/419; 600/407; 600/421; 378/4; 378/21

(58) Field of Classification Search
USPC ......... 600/407, 420, 421, 473, 476, 419, 425; 378/4, 21
See application file for complete search history.

(56) References Cited

U.S. PATENT DOCUMENTS 7,853,309 B2 * 12/2010 Ichihara et al. ............... 600/425
8,565,860 B2 * 10/2013 Kimchy et al. ............... 600/436

*Primary Examiner* — Unsu Jung
*Assistant Examiner* — Joel Lamprecht
(74) *Attorney, Agent, or Firm* — Takiguchi & Vogt, LLP

(57) ABSTRACT

The present invention relates to the field of medical imaging. More particularly, embodiments of the invention relate to methods, systems, and devices for imaging, including for tomography-based applications. Embodiments of the invention include, for example, a computed tomography based imaging system comprising: (a) at least one wide-beam grayscale imaging chain capable of performing a global scan of an object and acquiring projection data relating to the object; (b) at least one narrow-beam true-color imaging chain capable of performing a spectral interior scan of a region of interest (ROI) of and acquiring projection data relating to the object; (c) a processing module operably configured for: (1) receiving the projection data; (2) reconstructing the ROI into an image by analyzing the data with a color interior tomography algorithm, aided by an individualized gray-scale reconstruction of an entire field of view (FOV), including the ROI; and (d) a processor for executing the processing module. The extended interior methods and systems for spectral, optical, and photoacoustic imaging presented in this application can lead to better medical diagnoses by providing images with higher resolution or quality, and can lead to safer procedures by providing systems capable of reducing a patient's exposure time to, and thus quantity of, potentially harmful x-rays. Embodiments of the invention also provide tools for real-time tomography-based analyses.

12 Claims, 16 Drawing Sheets

Imaging geometry for collection of overlapped projections from two x-ray sources.

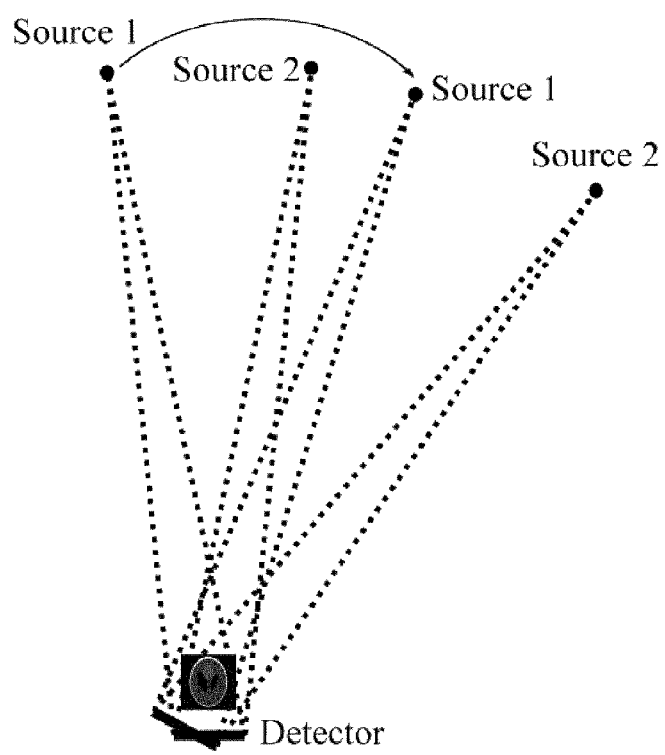
Figure 1. *Imaging geometry for collection of overlapped projections from two x-ray sources.*

FIG. 2A
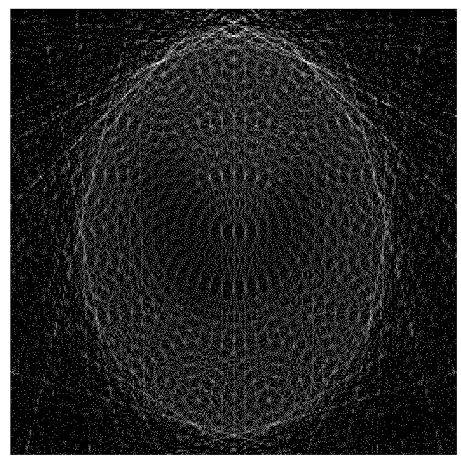
FIG. 2B
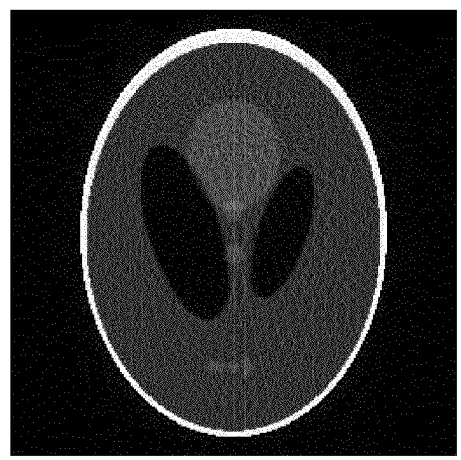
FIG. 2C
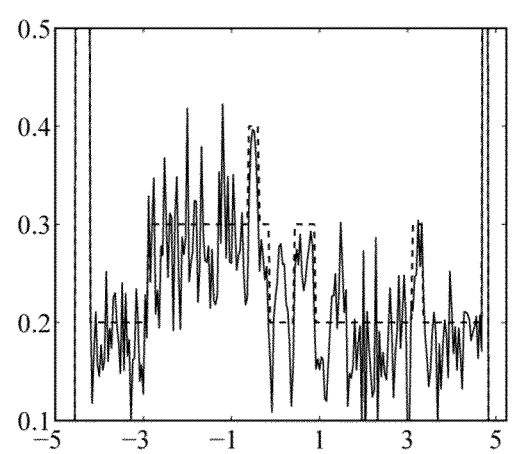
Figure 2.

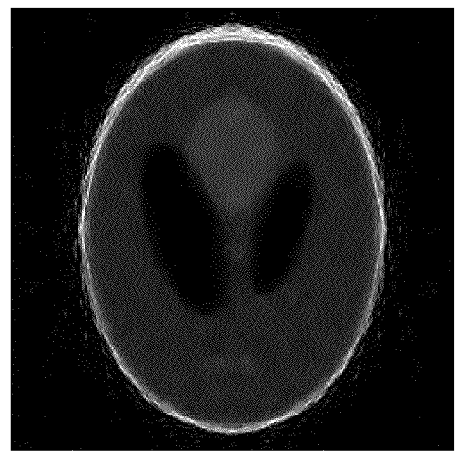
FIG. 3A
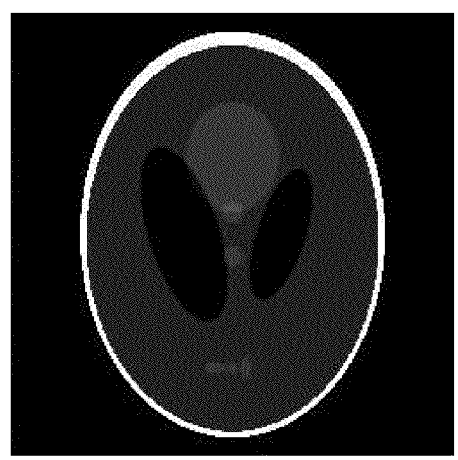
FIG. 3B
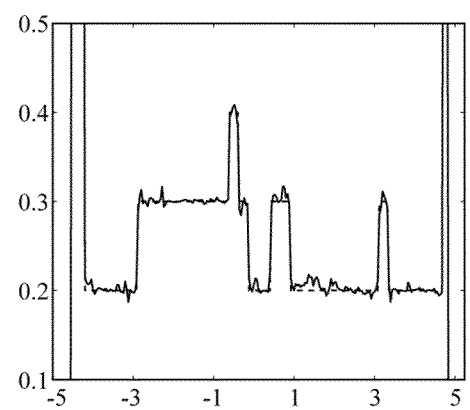
FIG. 3C
Figure 3.

FIG. 4A
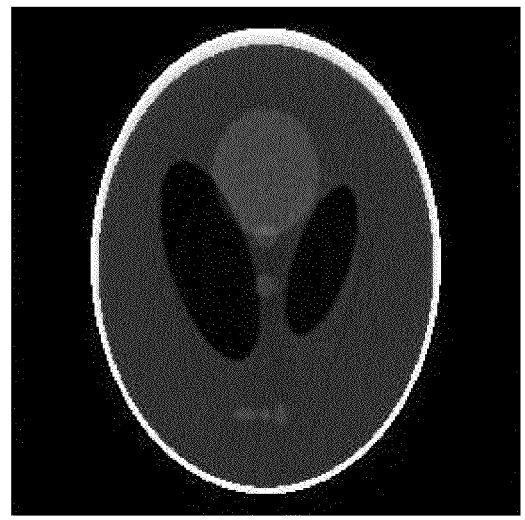
FIG. 4B
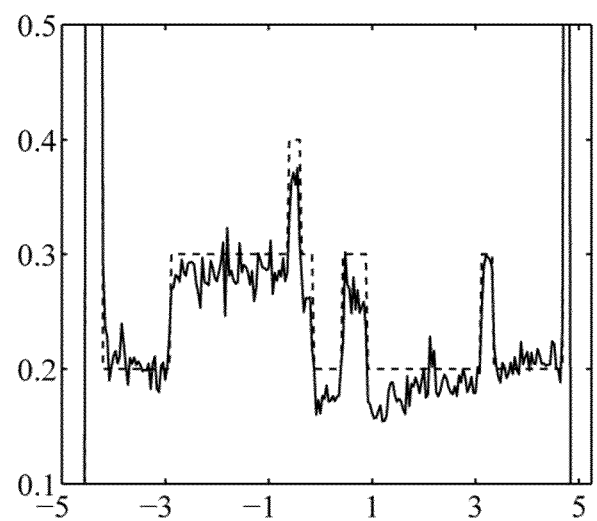
Figure 4.

Figure 5. *Convergence plots for (a) Test1, (b) Test2 and (c) Test3, with 3 linearization steps and 50 iterations after each linearization.*

Figure 6. *Convergence plots for (a) Test 1, (b) Test 2, and (c) Test 3, with 10 linearization steps and 3 iterations after each linearization step.*

|  | Energy (keV) | µ/ρ (cm²/g) | Jump Ratio |
|---|---|---|---|
|  | 11.8 | 75.8 |  |
| L3 | 11.9 | 187.0 | 2.5 |
|  | 13.6 | 128.3 |  |
| L2 | 13.7 | 176.4 | 1.4 |
|  | 14.3 | 158.8 |  |
| L1 | 14.4 | 183.0 | 1.2 |
|  | 80.6 | 2.1 |  |
| K | 80.7 | 8.9 | 4.2 |

FIG. 9A
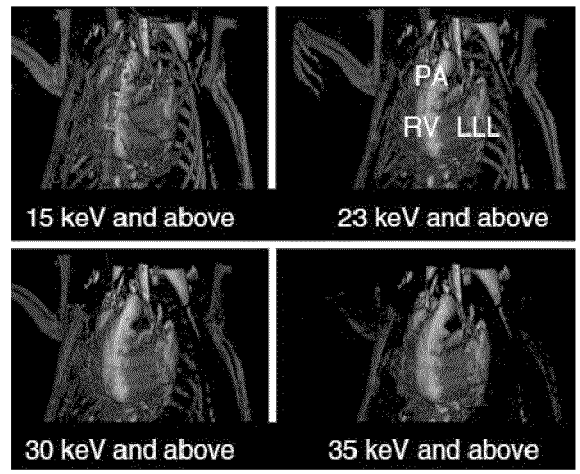
FIG. 9B
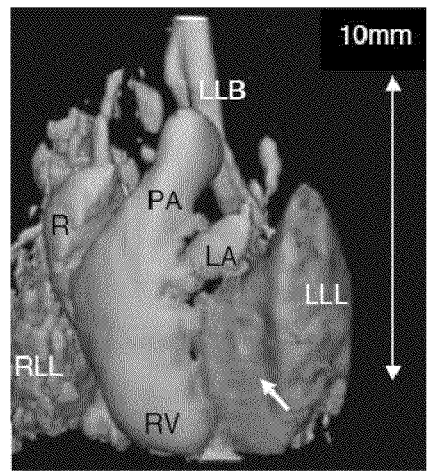
Figure 9.

FIG. 10A
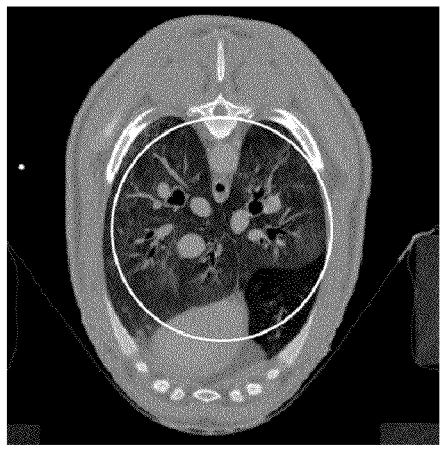
FIG. 10B
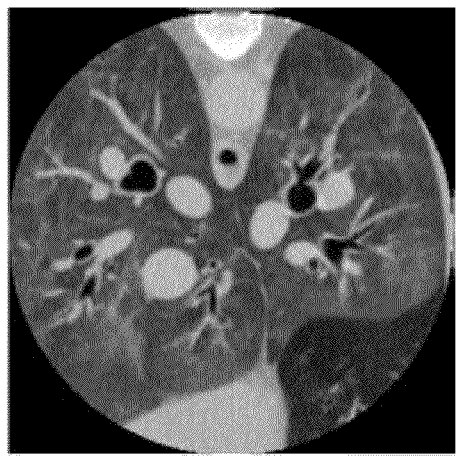
Figure 10.

Figure 13. *Hybrid true-color interior micro-CT - 3D rendering.*

Figure 14. *Top-level design of an exemplary photoacoustic tomography system for molecular imaging of an engineered blood vessel.*

EXTENDED INTERIOR METHODS AND SYSTEMS FOR SPECTRAL, OPTICAL, AND PHOTOACOUSTIC IMAGING

CROSS-REFERENCE TO RELATED APPLICATIONS

This application relies on the disclosure of and claims the benefit of the filing date of U.S. Provisional Application Nos. 61/260,543, filed Nov. 12, 2009; 61/260,566, filed Nov. 12, 2009; and 61/289,100, filed Dec. 22, 2009; the disclosures of each of which are incorporated by reference herein in their entireties.

STATEMENT OF GOVERNMENT INTEREST

This work was partially supported by the National Institutes of Health under NIH Grants EB001685, CA127189, CA135151, EB002667, EB004287, EB007288, and HL098912. The U.S. Government has certain rights in this invention.

BACKGROUND OF THE INVENTION

1. Field of the Invention

The present invention relates to the field of medical imaging. More particularly, embodiments of the invention relate to methods, systems, and devices for imaging, including for tomography-based applications.

2. Description of the Related Art

Existing CT schemes take projection data from an x-ray source being scanned along a trajectory and reconstruct an image from these data that are essentially line integrals through an object. In real-world applications, however, higher temporal resolution has been constantly pursued, such as for dynamic medical CT, and micro- and nano-CT. The multi-source scanning mode is well known to improve temporal resolution but the data acquisition and field of view are seriously restricted to avoid overlapped projections, such as in the case of the classic dynamic spatial reconstructor (DSA). Needed are methods of reconstructing an image using overlapped projection data, resulting in faster data acquisition without reducing image quality.

Small animal imaging is critically important in this post-genomic era. Currently, major efforts are being made in the fields of systems biology and medicine to link genomic and epigenetic features with complicated biological interactions such as phenotypic expression. Small animals, particularly genetically engineered mice, are often used as models of almost all human diseases. Over the past decade, there has been explosive growth in development of micro-imaging technologies to study small animals with emphasis on mice. At present, most all major biomedical research institutions and companies extensively use micro-imaging tools, including x-ray micro-CT, micro resonance imaging (micro-MRI), micro single photon emission computed tomography (micro-SPECT), micro positron emission tomography (micro-PET), ultrasound (US) and optical scanners.

Unique merits of x-ray micro-CT are evident relative to other micro-imaging modalities in the context of small animal imaging. In terms of imaging speed and cost-effectiveness, micro-CT is superior to magnetic resonance microscopy (MRM) and micro-MRI. Micro-CT captures much finer features than micro-PET and micro-SPECT, which is needed for accurate functional and molecular imaging. Micro-CT allows significantly deeper penetration than optical imaging, and much less artifacts than US. Two major limitations of current micro-CT techniques, however, are insufficient contrast resolution and high radiation dose.

Thus a need exists for spectrally-resolved photon-counting based methods, systems, and devices, which are capable of bright and colorful CT images for anatomical, functional, cellular and molecular imaging. Such imaging modalities are expected to lead to major healthcare benefits for diagnosis and treatment of cancers, cardiovascular diseases, and other pathologies.

Bioluminescence tomography (BLT) can be used to localize and quantify bioluminescent sources in a small living animal. Advancing planar bioluminescent imaging to the tomographic imaging framework, BLT helps detect gene expression, monitor therapies and facilitate drug development, among many other applications.

More particularly, BLT is used to reconstruct the bioluminescence source from the boundary measurement based on a physical model in which the optical parameters are unknown. The optical parameters and source, however, cannot be simultaneously reconstructed only from boundary measurement. Accordingly, what is needed is a modality fusion imaging methodology that can be used to recover the optical parameters using the photoacoustic imaging modality for a better forward modeling so that BLT reconstruction quality can be improved.

A major barrier to advancing tissue engineering research is our inability to monitor dynamic biological processes in a minimally invasive real-time fashion, which makes control and optimization extremely difficult. Current methods to assess tissue regeneration, such as histological and physiological analyses, are highly invasive and require destruction of the newly formed tissue, creating a fundamental knowledge discrepancy between cellular processes and whole organ biology. Thus, what is needed are minimally-invasive approaches for performing tomography-based procedures deep within tissue.

Further, many promising optical molecular imaging modalities, such as bioluminescence tomography, have a limited ability to detect deeply embedded optical molecular probes. Thus, what are needed are systems, methods, and devices using a sparsity-regularized computational optical biopsy (SCOB) approach for locating and quantifying the bioluminescent probes regardless of the source depth.

SUMMARY OF THE INVENTION

The inventors provide various methods, systems, and devices in this application, which are helpful for addressing some of the issues of existing tomography-based techniques.

Included in embodiments of the invention is a system for image reconstruction comprising: multiple sources for emitting x-rays to pass through a region of interest (ROI) of an object at multiple orientations; a detector array for receiving overlapping x-ray projection data from the multiple sources; a processing module operably configured for: receiving the overlapping x-ray projection data; and reconstructing the ROI into an image by: determining a difference between data relating to a first actual image and data relating to a second expected image of higher resolution than the first image; iteratively updating the expected data and iteratively updating the corresponding difference between the actual and expected data; performing a Taylor series expansion to linearize the imaging system by omitting high order terms; and performing POCS-gradient algorithm on this linearly approximated system iteratively; and a processor for executing the processing module.

Such a system can further be configured such that the multiple x-ray sources are operably configured for simultaneously emitting x-ray through the ROI of the object and wherein the detector is operably configured for simultaneously detecting the overlapping x-ray projection data. Even further, embodiments encompass configurations wherein the overlapped projections can be modeled as the sum of several exponential functions depending on the linear integral of the attenuation coefficients along the x-ray-source-detector path.

The invention also provides such a system, wherein the POCS-gradient algorithm employs a steepest gradient descent search method to reduce data discrepancy. Additionally, the system can be configured such that the POCS-gradient algorithm employs a steepest gradient descent search to minimize the object image total variation.

Embodiments of the present invention encompass methods of reconstructing an image comprising: emitting x-rays through a region of interest (ROI) of an object using multiple sources at multiple orientations to obtain overlapping x-ray projection data; detecting the overlapping x-ray projection data with a detector array; reconstructing the ROI into an image by: determining a difference between data relating to a first actual image and data relating to a second expected image of higher resolution than the first image; iteratively updating the expected data and iteratively updating the corresponding difference between the actual and expected data; performing a Taylor series expansion to linearize the imaging system by omitting high order terms; and performing POCS-gradient algorithm on this linearly approximated system iteratively; and reconstructing the ROI in image form.

Methods can include using multiple sources operably configured for simultaneously emitting x-ray through the ROI of the object and wherein the detector is operably configured for simultaneously detecting the overlapping x-ray projection data. Such methods can also be configured such that the overlapped projections can be modeled as the sum of several exponential functions depending on the linear integral of the attenuation coefficients along the x-ray-source-detector path.

The methods can be performed in a manner wherein the POCS-gradient algorithm employs a steepest gradient descent search method to reduce data discrepancy. The methods are also capable of being performed in a manner such that the POCS-gradient algorithm employs a steepest gradient descent search to minimize the object image total variation.

Other embodiments include a computed tomography based imaging system comprising: at least one wide-beam gray-scale imaging chain capable of performing a global scan of an object and acquiring projection data relating to the object; at least one narrow-beam true-color imaging chain capable of performing a spectral interior scan of a region of interest (ROI) of and acquiring projection data relating to the object; a processing module operably configured for: receiving the projection data; reconstructing the ROI into an image by analyzing the data with a color interior tomography algorithm, aided by an individualized gray-scale reconstruction of an entire field of view (FOV), including the ROI; and a processor for executing the processing module.

Such a system can be configured, wherein each imaging chain comprises an x-ray source and detector pair, and each pair is operably disposed on a common rotating slip ring. Additionally, systems of embodiments of the invention can further comprise multi-source interior true-color micro-CT for ultra-fast data acquisition. Systems can also be configured such that the imaging chains are operated simultaneously or sequentially or combination thereof.

More particularly, system embodiments include systems, wherein the interior tomography algorithm is further operably configured for: reconstructing the local images using the datasets from different energy levels; extracting features from reconstructed images of different energy levels. Another embodiment of the present invention may include a processing module operably configured for extracting features for volume information using the principal component analysis method.

Computed tomography based methods can also comprise: performing a global scan of an object and acquiring projection data relating to the object using at least one wide-beam gray-scale imaging chain; performing a spectral interior scan of a region of interest (ROI) of and acquiring projection data relating to the object using at least one narrow-beam true-color imaging chain; reconstructing the ROI into an image by analyzing the projection data with a color interior tomography algorithm, aided by an individualized gray-scale reconstruction of an entire field of view (FOV), including the ROI.

Such a method can be configured such that each imaging chain comprises an x-ray source and detector pair, and each pair is operably disposed on a common rotating slip ring. Other methods comprise multi-source interior true-color micro-CT for ultra-fast data acquisition.

The method of claim 8, wherein the imaging chains are operated simultaneously or sequentially or a combination thereof. Methods can also be performed in a manner, wherein the interior tomography algorithm is further operably configured for: reconstructing the local images using the datasets from different energy levels; extracting features from all the reconstructed images of different energy levels.

A method wherein the principal component analysis method is used to extract features for volume information can also be used.

Features of embodiments of the invention can include a photoacoustic tomography based bioluminescence tomography (BLT) imaging method for visualizing light absorbing structures comprising: receiving and processing photon propagation data of a bioluminescence source disposed inside an animal using BLT imaging; detecting signals from photoacoustically-induced ultrasonic waves resulting from absorption of light by tissue; reconstructing from the signals, the optoacoustic image $P(x)=\mu_a(x)\Phi(x)$, wherein $\mu_a(x)$ is optical absorption distribution and $\Phi(x)$ is local light fluence; performing optimization to obtain optical absorption and diffusion coefficients; reconstructing the bioluminescence source using a radiative transport equation or variant.

Further embodiments include methods of reconstructing into image form an interior region of interest (ROI) of an object comprising: administering an optical signal along a confocal line through an object in a manner such that the optical signal is capable of inducing generation of photoacoustic ultrasonic waves resulting from absorption of the optical signal by the object; rotating the object 360 degrees while administering the optical signal; at several intervals throughout the rotating, detecting signals from the photoacoustically-induced ultrasonic waves; reconstructing a photoacoustic image of the object from data relating to the photoacoustically-induced ultrasonic signals by using filtered back-projection.

Method embodiments may further comprise: administering the optical signal in a manner such that the confocal line crosses a region of interest (ROI) within the object; rotating the object in a manner such that the confocal line is capable of scanning the ROI; obtaining a truncated data set by filtering any time domain ultrasound signal to remove any signals exterior to signals relating to the ROI; reconstructing from the truncated data set, a photoacoustic image of the ROI using interior tomography techniques.

A photoacoustic tomography based system of the invention comprising: a processing module operably configured for: receiving data relating to photoacoustic ultrasonic signals resulting from absorption of an optical signal by tissue along a confocal line through the tissue; reconstructing a photoacoustic image from data relating to the photoacoustically-induced ultrasonic signals by using filtered back-projection; a processor for executing the processing module is also encompassed in various embodiments.

Such systems can be configured, wherein: the processing module is operably configured for: receiving data relating to a region of interest (ROI) within the tissue and relating to areas exterior of the ROI both of which the confocal line crosses; obtaining a truncated data set by filtering any time domain ultrasound signal to remove the signals relating to areas exterior to the ROI; reconstructing from the truncated data set, a photoacoustic image of the ROI using interior tomography techniques; a processor for executing the processing module.

Also encompassed by embodiments of the invention is an optical-biopsy-based photoacoustic tomography system comprising: a needle operably configured for delivering an optical signal from within an interior region of an object, such that the signal is capable of inducing generation of photoacoustic ultrasonic waves resulting from absorption of the optical signal by the object; a transducer or transducer array operably configured for detecting signals from the photoacoustically-induced ultrasonic waves; a processing module operably configured for receiving data from the transducer or transducer array and for reconstructing a photoacoustic image therefrom; and a processor for executing the processing module.

The systems can be configured to provide the transducer array disposed in the needle. Even further, the needle can be operably configured for delivering an optical signal into an engineered blood vessel wall.

Further embodiments include methods of reconstructing into image form an interior region of interest (ROI) of an object comprising: delivering an optical signal from within an interior region of an object, such that the signal is capable of inducing generation of photoacoustic ultrasonic waves resulting from absorption of the optical signal by the object; detecting signals from the photoacoustically-induced ultrasonic waves; reconstructing a photoacoustic image from data relating to the ultrasonic signals.

It is noted that although only specific embodiments or methods, systems, and devices are listed in this summary, these embodiments can be expanded to cover methods, systems, and/or devices regardless of the type of embodiment is listed. For example, when referring to only a method, such disclosure should be construed to include devices and systems comprising the same elements. Further, these specific embodiments can be altered or modified by omitting one or more elements specifically listed and/or by combining elements of another listed embodiment therewith. For example, if a method embodiment refers to having two method steps, that embodiment can be construed as a system capable of performing only one of those functions and/or as a system capable of performing both of the listed functions and any other function listed for another embodiment. It is within the capabilities of those of ordinary skill in the art to modify this disclosure in this way.

The features and advantages of the present invention will be apparent to those skilled in the art. While numerous changes may be made by those skilled in the art, such changes are within the spirit of the invention.

BRIEF DESCRIPTION OF THE DRAWINGS

FIG. 1 is a schematic diagram showing an exemplary set up for providing image reconstruction of an object from overlapping images of the object.

FIGS. 2A-B are images showing the difference between the ART and IROP reconstruction methods in the first test, Test 1.

FIG. 2C is a graph of the profiles along the central vertical line of the phantom, where the dotted and solid lines are, respectively, for the phantom and the IROP reconstruction of FIG. 2B.

FIGS. 3A-B are images showing the difference between the ART and IROP reconstruction methods in the second test, Test 2.

FIG. 3C is a graph of the profiles along the central vertical line of the phantom, where the dotted and solid lines are, respectively, for the phantom and the IROP reconstruction of FIG. 3B.

FIG. 4A is an image showing the IROP reconstruction method in Test 3.

FIG. 4B is a graph of the profiles along the central vertical line of the phantom, where the dotted and solid lines are, respectively, for the phantom and the IROP reconstruction of FIG. 4A.

FIGS. 9A-B are images of spectral micro-CT volumetric renderings differentiating contrast materials in a mouse.

FIGS. 10A-B are images of TV-minimization-based interior reconstruction of a sheep lung.

DETAILED DESCRIPTION OF VARIOUS EMBODIMENTS OF THE INVENTION

I. Image Reconstruction from Overlapped Projections

Figure 5A:
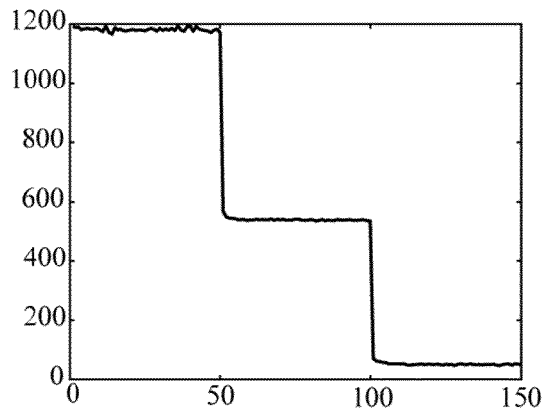
FIGS. 5A-C are graphs plotting the convergence of IROP in test 1, test 2 and test 3 with fewer linearizations and more iterations.

The inventors provide methods, systems, and devices capable of reconstructing an image from overlapped projections so that the data acquisition process can be shortened while the image quality remains essentially uncompromised. To perform image reconstruction from overlapped projections, the conventional reconstruction approach (for example, filtered backprojection (FBP) algorithms) cannot be directly used because of the two problems. First, overlapped projections represent an imaging system in terms of summed exponentials, which cannot be transformed into a linear form. Second, the overlapped measurement carries less information than the traditional line integrals. To meet these challenges, the inventors use a compressive sensing (CS) based iterative algorithm for reconstruction from overlapped data. This algorithm starts with a good initial guess, relies on adaptive linearization, and minimizes the total variation (TV). The feasibility of this algorithm has been demonstrated in numerical tests.

As shown in FIG. 1, the inventors provide methods, systems, and devices for reconstructing an image from overlapped projections so that a new dimension of freedom can be offered to design novel CT architectures.

Generally, in the overlapped projection geometry, two (or more) sources, for example A and B, emit x-rays simultaneously through an object to be reconstructed from various orientations. As a result, the resultant x-ray projections are overlapped onto the same detector array. The overlapped projections use the same detector array at the same time but complicate the imaging model. To perform image reconstruction from overlapped projections, the conventional reconstruction approach (for example, filtered backprojection (FBP) algorithms) cannot be directly used. First, overlapped projections represent an imaging system in terms of summed exponentials, which cannot be transformed into a linear form, since the x-ray intensity through an object follows an exponential decaying function. Second, overlapped measurement carries less information than the traditional line integrals, due to the additional uncertainty from mixing two ray sums, leading to an underdetermined imaging system.

Compressive sensing (CS) is a new technique being rapidly developed over the past years [1-2]. It has been shown that if a vector x contains at most S non-zero elements and there are K random measurements of x such that $K \geq C \cdot S \cdot \log(N)$, where C is a constant and N is the dimension of x, then minimizing the L−1 norm of x reconstructs x perfectly with an overwhelming probability. Inspired by its success in signal recovery, we propose a compressive sensing (CS) inspired iterative algorithm for reconstruction from overlapped data. This algorithm starts with a good initial guess, relies on adaptive linearization, and minimizes the total variation (TV).

According to embodiments of the invention, an image f can be discretized into a W by H matrix, which can be represented as a vector f of length $n = W \cdot H$. Let $N_{src}$ denote the total number of X-ray sources (for a dual-source system, $N_{src}=2$), $N_{bin}$ the total number of linear or area detector bins, and $N_{rot}$ the total number of view angles. The sampling process will yield $N_{bin} \cdot N_{rot}$ overlapped data. Since the x-ray attenuation is governed by an exponential decaying function, the overlapped projection data can be expressed as EQUATION (1):

$$p = \begin{bmatrix} p_{1,1} \\ p_{2,1} \\ \vdots \\ p_{N_{bin},1} \\ \vdots \\ p_{1,N_{rot}} \\ \vdots \\ p_{N_{bin},N_{rot}} \end{bmatrix} = \exp(-M_1 f) + \exp(-M_2 f) + \ldots + \exp(-M_{N_{src}} f)$$

$$= \begin{bmatrix} \exp(-M_{1,1,1} f) \\ \exp(-M_{1,2,1} f) \\ \vdots \\ \exp(-M_{1,N_{bin},1} f) \\ \exp(-M_{1,1,2} f) \\ \vdots \\ \exp(-M_{1,N_{bin},2} f) \\ \vdots \\ \exp(-M_{1,1,N_{rot}} f) \\ \vdots \\ \exp(-M_{1,N_{bin},N_{rot}} f) \end{bmatrix} + \begin{bmatrix} \exp(-M_{2,1,1} f) \\ \exp(-M_{2,2,1} f) \\ \vdots \\ \exp(-M_{2,N_{bin},1} f) \\ \exp(-M_{2,1,2} f) \\ \vdots \\ \exp(-M_{2,N_{bin},2} f) \\ \vdots \\ \exp(-M_{2,1,N_{rot}} f) \\ \vdots \\ \exp(-M_{2,N_{bin},N_{rot}} f) \end{bmatrix} + \ldots + \begin{bmatrix} \exp(-M_{N_{src},1,1} f) \\ \exp(-M_{N_{src},2,1} f) \\ \vdots \\ \exp(-M_{N_{src},N_{bin},1} f) \\ \exp(-M_{N_{src},1,2} f) \\ \vdots \\ \exp(-M_{N_{src},N_{bin},2} f) \\ \vdots \\ \exp(-M_{N_{src},1,N_{rot}} f) \\ \vdots \\ \exp(-M_{N_{src},N_{bin},N_{rot}} f) \end{bmatrix}$$

where p is an $N_{bin} \cdot N_{rot}$ by 1 vector whose element $p_{m,r}$, $m \in \{1, 2, \ldots, N_{bin}\}$ and $r \in \{1, 2, \ldots, N_{rot}\}$, is the overlapped projection datum detected by the $m^{th}$ detector bin at the $r^{th}$ view angle, $M_l$ denotes the system matrix for the $l^{th}$ source, $l \in$. The 1 by n row vector $M_{l,m,r}$ is the x-ray intersection length vector from the $l^{th}$ source to the $m^{th}$ detector bin at the $r^{th}$ view angle. The $k^{th}$ entry of $M_{o,n}$, is obtained by calculating the intersection length of the involved x-ray through the $k^{th}$ pixel of f, which corresponds to the indices l, m, and r.

The system matrix M and overlapped projection data can be readily computed in different ways. For example, in reference to [3], the following algorithm in Table 1 can be used to generate projection data:

TABLE 1

Algorithm 1 (Synthesis of Overlapped Projection Data)

Initialization:

Initialize the coordinates for the two sources and detector bins: $s_1, s_2, d$;
Define the rotation matrix $Q = I_{2 \times 2}$;
Zero-out the data vector p of size $N_{bin} \cdot N_{rot}$ by 1;
Specify the rotation angle increment θ;

TABLE 1-continued

Algorithm 1 (Synthesis of Overlapped Projection Data)

Synthesis:

Loop for k = 1: $N_{rot}$:
    With the current coordinates for the first source
    and the detector array,
    compute the system matrix $M_{1,k}$;
    With the current coordinates for the second source
    and the detector array,
    compute the system matrix $M_{2,k}$;
    Update the $k^{th}$ block of the data vector p:
        EQUATION (2)

$$p_k = \begin{bmatrix} p_{1,k} \\ p_{2,k} \\ \vdots \\ p_{N_{bin},k} \end{bmatrix} = \exp(-M_{1,k} f) + \exp(-M_{2,k} f)$$

Update Q:
        EQUATION (3)

$$Q = \begin{bmatrix} \cos(\theta) & -\sin(\theta) \\ \sin(\theta) & \cos(\theta) \end{bmatrix}$$

Update source and detector coordinates:
    $s_1 = Qs_1$;    EQUATION (4)
    $s_2 = Qs_2$;
    $d = Qd$;
End Next, the image can be reconstructed from the overlapped projection data. To alleviate the underdetermined measurement due to the overlapped nature of projection data, the compressed sensing (CS) principles is employed in the inventive reconstruction process. To utilize the sparsity of an underlying image, it is first transformed into a gradient counterpart, and then the L−1 norm of the gradient, which is known as the total variation (TV), is minimized, subject to the overlapped projection data. The entire reconstruction process can therefore be casted into a constrained nonlinear optimization problem:

Minimize: TV of f subject to $p = \exp(M_1 f) + \exp(M_2 f)$ and other constraints (such as intensity ranges and object features)

There are various ways to solve the above constrained TV minimization problem. In the CS field, a projection onto convex sets (POCS) and gradient descent search approach has been successfully used to solve this type of MRI and CT imaging problems [4-9]. POCS takes advantage of the fact that the linear constraints are hyper-planes in the n-dimensional space so that a closed form solution for the projection onto these hyper-planes can be derived. Such an algorithm works well in the single source geometry, because raw projection data can be processed into line integrals.

In the case of overlapped projections from two sources, however, the constraint equations, which are the sums of two exponentials, cannot be transformed into a linear form. Therefore, a different approach is needed. One solution is to make a good initial guess, such as a low-resolution CT image first. This blurry image will serve as a starting point, and the difference between this initial reference and the actual image will be iteratively updated, and at the same time the current guess will be also updated. Since the difference is assumed to be small, a Taylor series expansion can be performed to linearize the imaging system by omitting high order terms. Then, the POCS-gradient algorithm can be applied on this linearly approximated system iteratively.

Mathematically, let us denote f=g+df, where f is the original image, g the blurry image, and df the difference between f and g. Then, we have EQUATION (5):

$$p = \exp(-M_1 \cdot f) + \exp(-M_2 \cdot f) =$$
$$\exp(-M_1 \cdot g)\exp(-M_1 \cdot df) + \exp(-M_2 \cdot g)\exp(-M_2 \cdot df) =$$
$$\exp(-M_1 \cdot g)\left(\sum_{n=0}^{\infty} \frac{(-M_1 \cdot df)^n}{n!}\right) + \exp(-M_2 \cdot g)\left(\sum_{n=0}^{\infty} \frac{(-M_2 \cdot df)^n}{n!}\right) \approx$$
$$\exp(-M_1 \cdot g)(1 + (-M_1 \cdot df)) + \exp(-M_2 \cdot g)(1 + (-M_2 \cdot df)) =$$
$$\exp(-M_1 \cdot g) - \exp(-M_1 \cdot g)M_1 \cdot df +$$
$$\exp(-M_2 \cdot g) - \exp(-M_2 \cdot g)M_2 \cdot df.$$

That is, EQUATION (6):

$$[\exp(-M_1 \cdot g)M_1 + \exp(-M_2 \cdot g)M_2] \cdot df = p + \exp(-M_1 \cdot g) + \exp(-M_2 \cdot g).$$

Then, we have the approximate system EQUATION (7):

$$M_{new} df = p_{new},$$

$$M_{new} = \exp(-M_1 \cdot g)M_1 + \exp(-M_2 \cdot g)M_2,$$

where $p_{new} = p + \exp(-M_1 \cdot g) + \exp(-M_2 \cdot g)$. EQUATION (8).

The above approximate system is linear with respect to df. This linearity allows us to perform POCS on df. To perform the gradient descent search on the TV of g+df, we compute the gradient of the TV explicitly in the image domain, for example, using the formulas described in [8]. After the linearization with respect to df and the formulation of the TV gradient, we can apply the POCS-gradient algorithm to estimate df. Note that such a reconstructed image g+df can be used as a new guess in the POCS-gradient process until a satisfactory reconstruction is achieved, as summarized in the following reconstruction algorithm:

TABLE 2

Algorithm 2 (Image Reconstruction from Overlapped Projections (IROP))

Initialization:

df = 0;
g = A good initial guess, such as a blurry image from a low-resolution CT scan;
$N_{src} = 2$;
$N_{data} = N_{src} \cdot N_{bin} \cdot N_{rot}$;
$N_{linear}$ = A number of the system linearization steps;
$N_{itr}$ = A number of the POCS-gradient or SART-gradient iterations for each linear approximation;
$N_{grad}$ = A number of the gradient descent search steps;
a = A step size for the gradient descent search, say 0.2;
Obtain projection data using Algorithm 1 or from a real scan;

TABLE 2-continued

Algorithm 2 (Image Reconstruction from Overlapped Projections (IROP))

Reconstruction:

Linearization updating loop for I = 1: $N_{linear}$ (or until $\|p - \exp(M_1 g) - \exp(M_2 g)\|_p^q \le \epsilon$)
        Compute $M_{new}$;
        POCS-gradient (or SART-gradient) reconstruction loop for J = 1: $N_{itr}$.
        For $POCS_{itr}$ = 1: $N_{data}$
            Project df onto the constraint equation:

$$df = df - M_{new} \frac{p_{new} - M_{new} df}{\|M_{new}\|^2};  \quad\quad \text{EQUATION (9)}$$

End
        For $GRAD_{itr}$ = 1: $N_{grad}$
            Compute the TV with respect to df;
            Perform the gradient descent search;
        End
    End
    Update the current guess g = g + df ;          EQUATION (10)
End To demonstrate the feasibility of the algorithm for image reconstruction from overlapped projections, a program in MATLAB was developed, which implemented the traditional algebraic reconstruction technique (ART) for comparison. A Modified 2D Shepp-Logan phantom was scaled into a 5 cm by 5 cm square and discretized into a 256×256 matrix. This data is illustrated in Table 3.

TABLE 3

Parameters of the 2D modified Shepp-Logan phantom.

| Axis length( a, b ) | Center ( x, y ) | Angle ( θ ) | Density |
|---|---|---|---|
| (0.690, 0.92) | (0, 0) | 0 | 1.0 |
| (0.6624, 0.874) | (0, −0.0184) | 0 | −0.8 |
| (0.11, 0.31) | (0.22, 0) | −18 | −0.2 |
| (0.16, 0.41) | (−0.22, 0) | 18 | −0.2 |
| (0.21, 0.25) | (0, 0.35) | 0 | 0.1 |
| (0.046, 0.046) | (0, 0.1) | 0 | 0.1 |
| (0.046, 0.046) | (0, −0.01) | 0 | 0.1 |
| (0.046, 0.023) | (−0.08, −0.605) | 0 | 0.1 |
| (0.023, 0.023) | (0, −0.606) | 0 | 0.1 |
| (0.023, 0.046) | (0.06, −0.606) | 0 | 0.1 |

The phantom was centered at the origin of the reconstruction coordinate system. A circular scanning trajectory of radius 121.66 cm was assumed with the two sources initially located at (−20 cm, 120 cm) and (20 cm, 120 cm) respectively. A 14 cm long linear detector array was positioned opposite to the sources and 5 cm below the phantom with a distance of 131.53 cm from each of the sources. Gaussian white noise was drawn from the normal distribution N(0, 0.005) and added to ideal projection data during the sampling stage. The scanning geometry is illustrated in FIG. 1. Other parameters are listed in Table 4.

TABLE 4

Parameters used in the numerical tests.

|  | Test 1 | | Test 2 | | Test 3 | |
|---|---|---|---|---|---|---|
|  | ART: Single Source | IROP: Two Source | ART: Single Source | IROP: Two Source | ART: Single Source | IROP: Two Source |
| $N_{rot}$ | 15 | 150 | 30 | 150 | NA | 150 |
| $N_{bin}$ | 50 | 500 | 100 | 500 | NA | 500 |

TABLE 4-continued

Parameters used in the numerical tests.

|  | Test 1 | | Test 2 | | Test 3 | |
|---|---|---|---|---|---|---|
|  | ART: Single Source | IROP: Two Source | ART: Single Source | IROP: Two Source | ART: Single Source | IROP: Two Source |
| $N_{linear}$ | NA | 3 | NA | 3 | NA | 3 |
| $N_{itr}$ | 50 | 50 | 50 | 50 | NA | 50 |
| $N_{grad}$ | NA | 5 | NA | 5 | NA | 5 |

Both ART and IROP reconstructions were performed under these conditions, with blurry and constant initial guess. Representative results are provided in FIGS. 2 through 4. It has been observed that the IROP algorithm would work well if the initial guess resembles the ideal image through a moderate blurring process. Actually, in the first test the blurry images were obtained by blurring a low-quality ART image reconstructed under a severely under-sampling condition with only $N_{bin} \times N_{rot} = 15 \times 50 = 750$ measurements to reconstruct $256 \times 256 = 65536$ pixels. In the second test, more measurements were made in the single source scan, and the IROP reconstruction became better. Also, the IROP reconstruction tended to be smoother than the corresponding ART images, indicating that compressed sensing (CS) is more effective than ART in suppressing image noise. In the last test, an IROP image was reconstructed with a constant initial guess (an zero image). It is apparent that the reconstructed image can be further improved if more iterations are used.

Figure 5B:
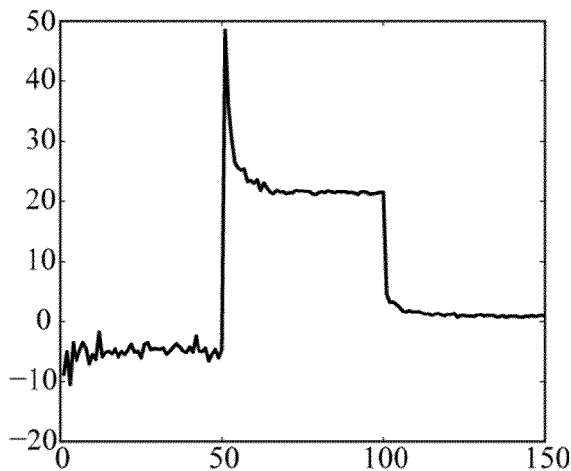
Figure 5C:
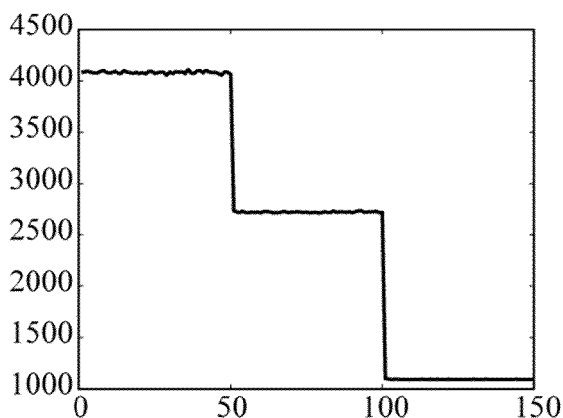

To investigate the convergence of IROP, we first introduce an evaluation metric (n), which is defined as the sum of the component values in the error vector df at $n^{th}$ iteration:

$$\delta(n) = \sum_{i=1}^{256^2} df_i(n) \quad\quad \text{EQUATION (11)}$$

where the subscript i denotes the $i^{th}$ pixel component in the error vector df. We then plotted δ(n) for every iteration. The results for each of the three tests are shown in FIG. 5. There are mainly three important observations from the convergence plots. First, the big jumps at multiples of $N_{itr}$ indicates that linearization step played an important role in the convergence of IROP. Second, as IROP goes through more iterations, δ(n) approaches zero, showing that IROP effectively reduces the differences between the original and the reconstructed images. Additionally, the smaller values for δ(n) in test 2 show that a good initial guess can lead to better reconstruction quality.

Figure 6A:
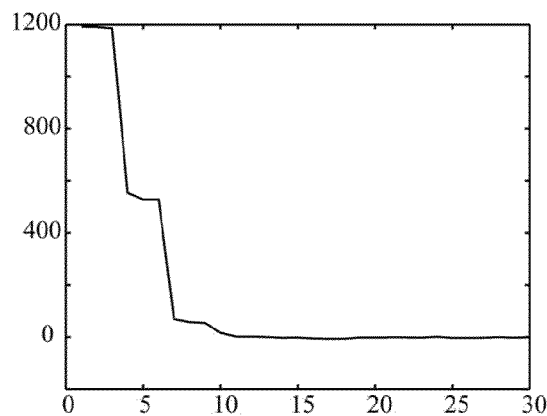
FIGS. 6A-C are graphs plotting the convergence of IROP in Tests 1, 2, and 3 with fewer iterations and more linearizations.
Figure 6B:
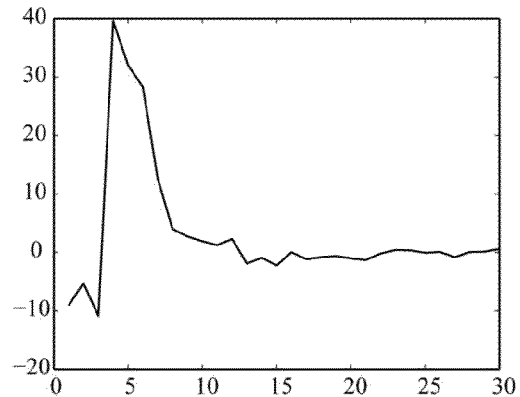
Figure 6C:
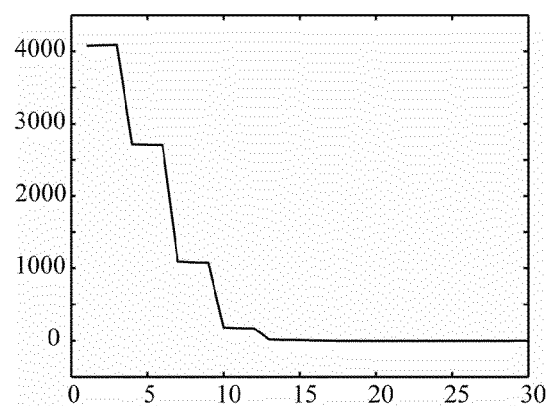

FIG. 6 shows another 3 plots obtained with fewer iterations and more linearizations. It is observed that the error between the reconstructed image and the true image was reduced dramatically immediately after each new linearization. After 3 or 4 linearization processes, the convergence curve became stable and smooth. After that, if the number of iterative steps in each linearization process was increased, the image quality would be improved only slowly. Hence, to balance of image quality and computational time a good solution is for the method to use a limited number of iterative steps after each earlier linearization process, and perform a sufficiently large number of iterative steps after the final linearization, for example, after 3 or 4 linearization processes.

One notable advantage of the IROP scheme is to improve the data acquisition speed. In one exemplary application, we can assume that the two sources are fairly close so that the detector collimation can work effectively for both the sources. If a good number of sources are used, scattering effects could be a concern. In that case, scattering correction may be needed using hardware (such as some degree of multiplexing) and/or software (such as model- or image-based compensation) methods [10-13].

Using Algorithm 2, to ensure success of the linearization, a good initial guess should be employed. It is underlined that it is practical to have such a good guess. For example, in multi-resolution CT studies a low resolution image serves as a guess naturally. Also, in dynamic CT studies, an initial image represents a good guess to subsequent images. When we have a cluster of computers, we may use multiple random initial guesses to search for a more accurate and stable reconstruction. Furthermore, Algorithm 2 may be adapted into an evolutionary scheme.

The implementation of Algorithm 2 can be improved in several ways. To reduce the smoothing artifact, one can reduce the number of gradient descent iterations or the step size. Other algorithmic parameters could also be tuned for a specific type of applications. Most importantly, the computational structure of Algorithm 2 is based on simple heuristics, and does not reflect all the constraints and requirements in a well integrated and optimized fashion.

It is believed that the global convergence of the IROP scheme can be established if a guess is appropriately chosen, as numerically shown above. Actually, the IROP problem is much better posed than many well-known inverse problems such as diffuse optical tomography (DOT) [14]. In IROP with two sources, each datum reflects information from two lines. In DOT, each measure is related to a random zigzag trajectory. Thus, it is not surprising to see better results with IROP than that with DOT. When we have infinitely many sources along a line, we have a line-source imaging geometry, which has been studied by Bharkhada [15] and still yields better results than DOT reconstruction [15].

Since the IROP scheme mixes line integrals pair-wise, the IROP problem may lead to an underdetermined system of measurement equations, especially when the number of samples is not sufficiently large for ultrafast imaging performance. To address this issue, we have implemented the CS principles in Algorithm 2 by minimizing the TV. CS is a contemporary technique for solving an underdetermined system of linear equations, whose solution is known to be sparse. The main idea is to minimize cardinality, or equivalently to minimize the TV in many cases. In the context of IROP, an image itself is usually not sparse, but it can be sparsified in a transformed domain such as the gradient transform, and then we can apply the L−1 norm minimization in the transformed domain subject to the projection data constraints for good reconstructions, as numerically shown in the preceding section.

The inventive IROP approach can be extended to multiple other imaging scenarios. In transmission ultrasound imaging multiple ultrasound sources can be used with a single array of detectors (transducers). This may be also related to the area of signal unmixing. The common task would be to unravel an underlying signal or image from mixed measures.

E. Candès: Compressive Sampling, Int. Congress of Mathematics, 3:1433-1452, Madrid, Spain, 2006.

D. Donoho, Compressed Sensing, IEEE Trans. on Information Theory, 52(4), pp. 1289-1306, 2006.

R. Siddon: Fast calculation of the exact radiological path for a three-dimensional CT array. Medical Physics 12:252-255, 1985.

Candes E J and Romberg J: Signal recovery from random projections Computational Imaging III, Proc. SPIE 5764:76-86, 2005.

Candes E J, Romberg J and Tao T: Robust uncertainty principles: exact signal reconstruction from highly incomplete frequency information. IEEE Trans. Inf. Theory 52:489-509, 2006.

Sidky E Y, Kao C M and Pan X C: Accurate image reconstruction from few-views and limited-angle data in divergent-beam CT. J. X-ray Sci. Technol. 14:119-39, 2006.

Chen G H, Tang J and Leng S: Prior image constrained compressed sensing (PICCS): a method to accurately reconstruct dynamic CT images from highly undersampled projection data sets. Med. Phys. 35:660-3, 2008.

Yu H, Wang G: Compressive sensing based interior tomography. Physics in Medicine and Biology, 54:2791-2805, 2009.

Yu H, Yang J S, Jiang M, Wang G: Supplemental analysis on compressed sensing based interior tomography. PMB 54:N425-N432, 2009.

L. Zhu, et al., "Scatter correction for cone-beam CT in radiation therapy," Medical Physics, vol. 36, p. 2258, 2009.

Y. Kyriakou and W. Kalender, "Efficiency of antiscatter grids for flat-detector CT," Physics in Medicine and Biology, vol. 52, pp. 6275-6293, 2007.

J. Siewerdsen, et al., "A simple, direct method for x-ray scatter estimation and correction in digital radiography and cone-beam CT," Medical Physics, vol. 33, p. 187, 2006.

G. Poludniowski, et al., "An efficient Monte Carlo-based algorithm for scatter correction in keV cone-beam CT," Phys. in Medicine and Biology, vol. 54, pp. 3847-3864, 2009.

D. Boas, et al., "Imaging the body with diffuse optical tomography," IEEE Signal Processing Magazine, vol. 18, pp. 57-75, 2001.

Bharkhada D, Yu H, Liu H, Plemmons R, Wang G: Line-Source Based X-Ray Tomography. International Journal of Biomedical Imaging Volume 2009 (2009), Article ID 534516, 8 pages doi:10.1155/2009/534516.

II. Color Diffusing Interior Tomography.

A. Spectral Micro-CT. [Photon-counting Technology]. X-ray detection technology can be categorized into two groups: energy-integration and photon-counting. Almost exclusively, all current x-ray scanners use energy-integrating detectors where electrical signals, from interactions between an x-ray beam and materials, are accumulated over an entire spectrum. In contrast, photon-counting detectors recognize photons both individually and spectrally. The advantages of photon-counting detectors are evident relative to energy-integrating detectors (Jakubek 2009). First, photon-counting detectors record spectral responses of materials that are invisible to energy-integrating detectors. In energy-integrating detectors, low-energy photons carry more contrast information but receive lower weights due to beam hardening. Photon-counting detectors should not have any such bias in weighting x-ray photons (Cahn, Cederstrom et al. 1999; Giersch, Niederlohner et al. 2004). Second, photon-counting detectors have an inherently higher signal-to-noise ratio (SNR) by utilizing spectral information, suppressing electronic and Swank noise (Swank 1973) and rejecting scattered photons (Shikhaliev 2005). The SNR improvement for photon-counting detectors can be up to 90% (Giersch, Niederlohner et al. 2004). Third and most importantly, photon-counting detectors can reveal elemental composition of materials and support novel contrast-enhanced studies (Schlomka, Roessl et al. 2008; Anderson, Butler et al. 2010) and opening new possibilities for functional, cellular and molecular imaging with novel contrast agents such as gold nano-particles (Akolekar, Foran et al. 2004; Hainfeld, Slatkin et al. 2006; Xu, Tung et al. 2008; Wang, Wu et al. 2010).

[Medipix Detector Family]. Medipix is a series of state-of-the-art photon-counting detectors for x-ray micro-imaging from the CERN collaboration (Campbell, Heijne et al. 1998). Medipix1 has detector cells each measuring 170×170 μm$^2$ (Campbell, Heijne et al. 1998); Medipix2 refines that to 55×55 μm$^2$ (Llopart, Campbell et al. 2002). The performance of Medipix2 is limited by the charge cloud effect over neighboring pixels which compromises energy resolution much more than spatial resolution. To address this issue, another system is needed which has special circuitry for each pixel to allow charge deposition to be analyzed without spectral distortion. The readout logic should be configured to support eight energy thresholds for spectroscopic imaging. It is underlined that the Medipix design allows use of various detection substrates including Si, GaAs, and CdTe for pre-clinical and clinical x-ray energy ranges (Zwerger, Abu-Id et al. 2007; Sorgenfrei, Greiffenberg et al. 2008).

[MARS Micro-CT Scanner]. With its unique Medipix detectors, the state-of-the-art true-color micro-CT scanner—Medipix All Resolution System (MARS)—has been designed and produced by MARS Bioimaging Ltd. The gantry of this system allows a full-scan with an x-ray source (SourceRay—SB80-1k 80 kV) and spectral camera assembly under precise control around a specimen or animal up to 100 mm in diameter and 300 mm in length. The customized camera has a MARS gigabit readout accommodating up to six Medipix2 or Medipix3 detectors.

[Biomedical Applications]. Due to its energy-resolving power, high SNR, fine spatial resolution and fast readout speed, Medipix and MARS CT techniques have found a wide range of exciting applications in radiography (Greiffenberg, Fiederle et al. 2009), phase-contrast imaging (Jakubek, Granja et al. 2007), breast CT (Frallicciardi, Jakubek et al. 2009), and micro-CT including x-ray fluorescence analysis (Dammer, Frallicciardi et al. 2009; Firsching, Butler et al. 2009; Jakubek 2009). It is underlined that the utility of spectral CT can be dramatically boosted with novel contrast agents such as gold nano-particles for functional, cellular and molecular imaging.

Figures 7, 7A, 7B:
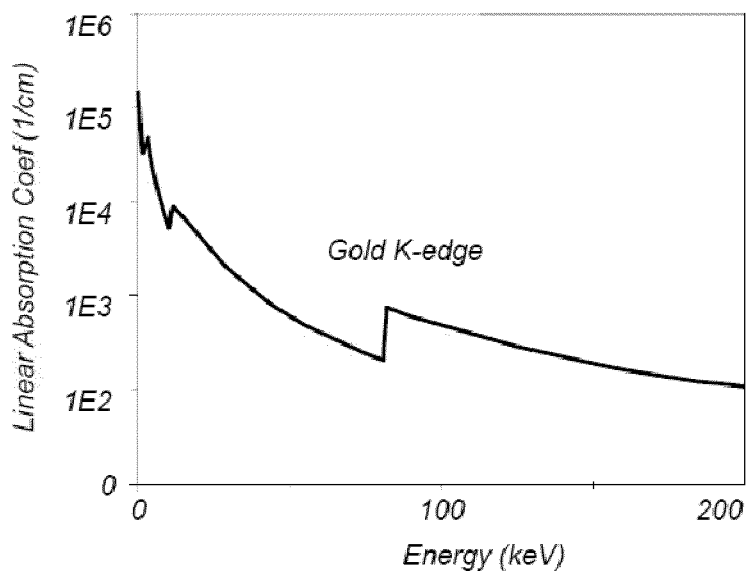
FIG. 7A is graph showing the absorption characteristics of Gold as a function of x-ray photon energy.
FIG. 7B is table showing the absorption characteristics of Gold as a function of x-ray photon energy.

For example, AuroVist™ is the first gold nano-particle x-ray contrast agent for in vivo small animal imaging, enabling greatly enhanced x-ray imaging of tumors, blood vessels, and other structures. It consists of 1.9 or 15 nm gold nano-particles with a water soluble organic shell for high concentration (up to 1.5 g Au/cc) and is well tolerated by animals. Major gains with AuroVist™ include significantly higher contrast and longer residence time than iodine agents, clearance through kidneys with low toxicity (LD50>1.4 g Au/kg), and, most excitingly, spectral imaging (such as K-edge imaging as shown in FIG. 7). Clearly, potential applications of spectral CT are important, immediate and numerous.

B. Color Interior Tomography. [Interior Tomography]. While classic CT theory targets exact reconstruction of a whole cross-section from complete projections, biomedical applications of CT and micro-CT often focus on much smaller internal regions of interest (ROIs), such as cardiac structures. Classic CT theory cannot exactly reconstruct an internal ROI from truncated x-ray projections that only pass through the ROI because this interior problem does not have a unique solution (Natterer 2001). When applying traditional CT algorithms for interior reconstruction from truncated projections, features outside the ROI may create disturbing artifacts overlapping internal features, rendering the images inaccurate or useless. Over the past decade, lambda tomography has developed as a branch of applied mathematics that recovers gradient-like features within an ROI from localized data (Faridani, Ritman et al. 1992; Ramm and Katsevich 1996; Faridani, Finch et al. 1997; Quinto 2007; Quinto and Oktem 2007; Yu, Wei et al. 2007). However, the outcomes of lambda tomography are not appealing in biomedical applications because of their non-quantitative nature.

Figure 8:
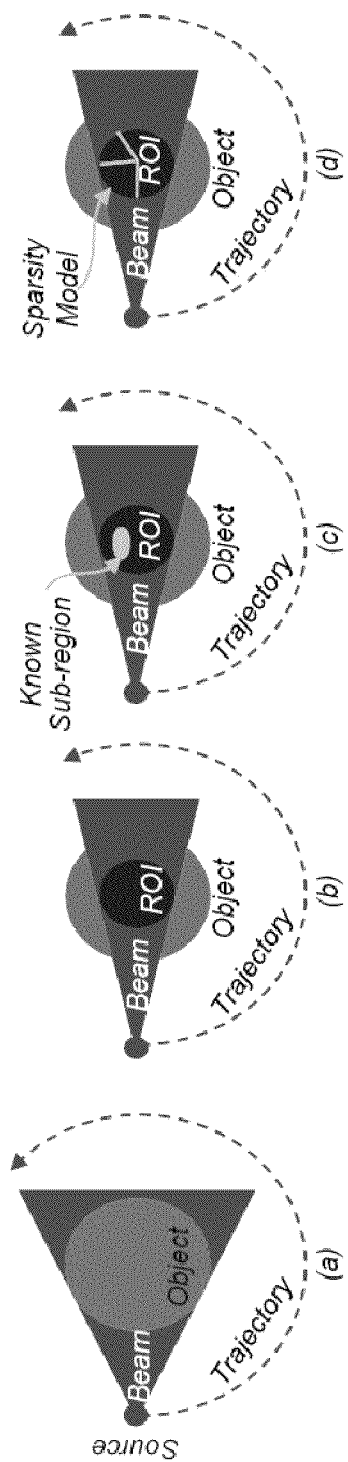
FIGS. 8A-D are illustrations depicting ROI reconstruction using the interior tomography approach.

Previously, the inventors have shown that the interior problem can be exactly and stably solved if a sub-region in the ROI is known (Ye, Yu et al. 2007a; Ye, Yu et al. 2007b; Ye, Yu et al. 2008a; Yu, Ye et al. 2008b) (FIG. 8). Similar results were also reported by Kudo et al. (Kudo, Courdurie et al. 2007; Kudo, Courdurier et al. 2008). Precise knowledge of a sub-region is available if we have air gaps, water, blood or other quantitative landmarks in the ROI. More generally, such prior knowledge can be acquired in sequential, dynamic, or multi-resolution studies. However, it can be difficult to obtain precise prior knowledge of a sub-region in important cases such as perfusion cardiac CT or micro-CT of live mice (used as a model for human cardiovascular diseases).

[Compressive Sensing]. The classic Nyquist sampling theorem states that one must sample a signal at least twice as fast as its bandwidth to capture all the information. Surprisingly, an emerging theory—compressive sensing (CS)—was recently developed to capture compressible signals at a sampling rate much below the Nyquist rate and allow accurate reconstruction of these signals from sparse samples (Candes, Romberg et al. 2006; Donoho 2006). The main idea of CS is that most signals are sparse in an appropriate orthonormal system; that is, a majority of their expansion coefficients are close or equal to zero. Typically, CS starts by taking a limited amount of samples, using a least correlated measurement matrix, and then the signal is exactly recovered with an overwhelming probability from the limited data via the $l_1$ norm minimization. Since samples are insufficient in the traditional sense, recovering the signal would involve an under-determined matrix equation. That is, there are many candidate solutions that can fit the limited dataset. Thus, some additional constraint must be enforced to select the "best" candidate. While the classical solution to such inverse problems is to minimize the $l_2$ norm, it was shown that finding the candidate with the minimum $l_1$ norm, which is closely related to the total variation (TV) minimization in a number of imaging cases (Rudin, Osher et al. 1992), is the most reasonable choice (Candes, Romberg et al. 2006; Donoho 2006). Inspired by this, the inventors previously proved that exact interior reconstruction is achievable with an interior scan if an ROI is piecewise constant or polynomial (Wang and Yu 2008; Han, Yu et al. 2009; Yu and Wang 2009; Yu, Yang et al. 2009), which suggests that interior tomography can be accurately achieved in the CS framework without precise knowledge of a sub-region in the ROI. This interior tomography approach is shown in FIG. 8.

[Hybrid Spectral CT]. Advantages of systems, methods, and devices of the present invention include a boost in conventional micro-CT performance with a powerful internal spectral imaging capability without significant increment to engineering cost and radiation dose. First, it is apparent that a widely applicable micro-CT scanning mode should combine one conventional global scan with one or more spectral local/interior scans. Thus, embodiments of the invention provide a first-of-its-kind hybrid micro-CT system. Second, the inventive systems demonstrate a cost-effective transition from conventional gray-scale to true-color (multi-spectral) micro-CT. Currently, high-end spectral detectors for micro-CT, such as Medipix3, are rather expensive; the inventive narrow-beam spectral imaging chain is expected to be much more affordable to fabricate and maintain while minimizing radiation dose and scattering artifacts from partial beams outside an ROI. Third, this hybrid system can be empowered by color interior tomography algorithms that produce accurate and stable spectral interior reconstruction, aided by a new type of prior knowledge—an individualized gray-scale reconstruction of an entire field of view (FOV), including an ROI.

Since Hounsfield's Nobel Prize winning work decades ago, CT systems have traditionally collected photon-integrating data and produced gray-scale images in so-called "Hounsfield unit (HU)". Furthermore, CT architectures have been dictated by large width detector arrays to fully cover a transverse slice, even though most applications are energy-dependent and ROIs are often small parts of the whole cross-sections or volumes. The fundamental reasons behind such single channel imaging and large detector width have been the lack of high-performance spectral detection and inability to produce exact interior reconstructions (until recently). Embodiments of the present invention make solid steps forward from gray-scale to true-color CT imaging and from wide detector-based architectures to locally oriented scanning architectures. The integration of these components provides a highly powerful and innovative new CT architecture.

MARS Micro-CT Results. [High-Resolution True-color Detectors]. The Medipix family of energy-selective photon-counting detectors is being actively developed, which represents state-of-the-art of color x-ray detection technology for clinical and preclinical CT. The unique features include high resolution, low noise and fast speed. Medipix2 allows the selection of a single energy window. Medipix3 enables simultaneous data acquisition in up to 8 spectral channels or energy bins. Medipix2 and Medipix3 chips have 256×256 pixels in an active area of 14×14 mm$^2$. Each pixel is 55×55 µm$^2$. The detector's application-specific integrating circuit (ASIC) is a complementary metal-oxide semiconductor (CMOS) chip. This is bump-bonded onto another semi-conducting sensor. Each photon interacting with the sensor creates a charge cloud to be analyzed by the underlying CMOS ASIC. These detectors can cover larger areas by tiling into arrays, which are rather expensive.

The Medipix technology holds great promise for both preclinical and clinical applications. Medipix allows a choice of a sensor layer to be bonded on the CMOS ASIC, depending on the imaging requirements. Silicon (Si) is chosen for its high uniformity and affability for preclinical applications although it only has a quantum efficiency up to 35 keV. Cadmium Telluride (CdTe), on the other hand, has a quantum efficiency up to 100 keV, suitable for clinical applications. However, CdTe is currently difficult to produce with high homogeneity, compromising the energy and spatial resolution of the detector assembly.

[True-color Micro-CT Results]. A gigabit Ethernet readout has been built for the Medipix detectors. The readout can write the detector's pixel configuration and read the pixel counters at up to 100 Hz. This readout may hold up to 6 Medipix2 detectors in a 2×3 array. The complete assembly of the readout and Medipix detectors comprises a MARS camera and is mounted on a MARS-CT gantry with a conventional X-ray tube operated at 75 kVp and 150 µA. To showcase 3D spectral images of small animals, a MARS-CT system was used to scan 6 black mice (C57BL/6) after injection of iodinated contrast material and barium sulphate into the vascular system, alimentary tract and respiratory tract while the mice were being euthanized. The mice were preserved in resin and imaged at four energy levels from 12 to 42 keV to include the K-edges of iodine (33.0 keV) and barium (37.4 keV). These images of <55 µm isotropic voxels were produced. Principal component analysis was applied to identify independent energy responses and distinguish the contrast agents with the K-edges only 4 keV apart. As shown in FIG. 9, the conspicuity of the bone decreases as keV increases, whereas the iodine (in right heart and pulmonary vessels) increases in conspicuity up to 30 keV, and barium (in left lower lobe bronchi and both lower lobes) increases in conspicuity up to 35 keV. This would be hardly differentiated on conventional gray-scale micro-CT images.

Interior Tomography Results. [Gray-scale Interior CT Demo]. To demonstrate the feasibility of interior tomography, a sheep lung CT study has been performed. A fan-beam dataset was acquired on a Siemens CT scanner (100 kVp, 150 mAs). A global image was reconstructed using the commercial FBP method. In reference to the globally reconstructed image, an example ROI was arbitrarily specified. To evaluate the capability of our subregion-knowledge-based interior tomography approach (Ye, Y., H. Yu, et al. 2007), the global filtered backprojection (FBP), optimal local FBP, optimal order-subset (OS) simultaneous algebraic reconstruction technique (SART), and interior tomography reconstruction, were systematically compared and demonstrated clear superiority of interior tomography (see Wang, G., H. Yu, et al. 2009). To show the feasibility of the TV-minimization-based interior tomography (Wang, Yu et al. 2009; Yu and Wang 2009), projection data through the ROI was kept. As shown in FIG. 10 (recently published in PNAS), the inventive interior tomography algorithm performed very well (Wang and Yu 2010).

Figure 11:
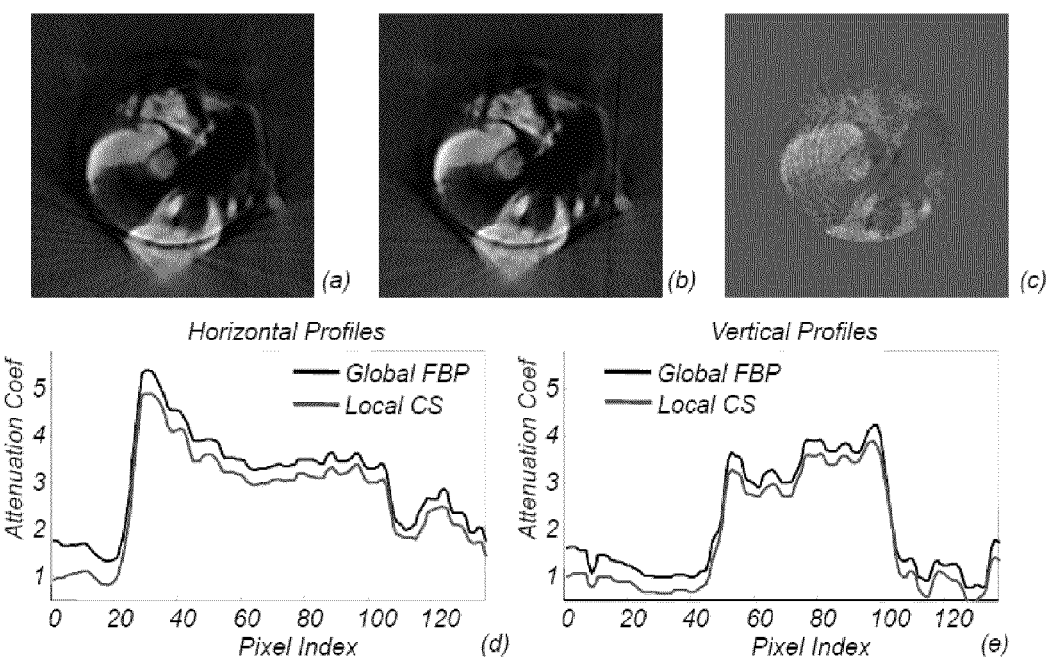
FIGS. 11A-C are images of TV-minimization-based spectral interior reconstruction.
FIGS. 11D-E are graphs of the profiles from the global FBP and TV-minimization-based interior reconstructions through the center of the ROI.

[True-color Interior Micro-CT Demo] The inventors analyzed a spectral micro-CT dataset collected at energy thresholds of 23, 30 and 35 keV. Individual spectral interior reconstructions were performed using the inventive TV-minimization-based interior tomography algorithm (Yu and Wang 2009). FIG. 11 presents the representative results. It is clearly observed that the total-variation-based interior reconstructions match the global FBP reconstruction quite well. The remaining discrepancy and artifacts can be addressed using other aspects of the present invention described in detail below.

Hybrid Micro-CT Prototyping. Given the novel and potential applications of x-ray spectral micro-CT for tissue characterization, functional studies, cellular and molecular imaging, the graduate transition from gray-scale to true-color micro-CT is certain sooner or later. However, there are two major challenges in this process: detector cost and radiation dose. First, the spectral detection technology is not yet mature, especially for large area, high resolution, uniform performance and long operation. The replacement of a gray-scale x-ray detector array with a true-color spectral camera will be rather expensive in the near future. Second, radiation exposure has been a public concern, and x-ray spectral detection would require much higher radiation dosage if each spectral channel receives the same number of photons as that for the corresponding photon integrating mode.

Figure 12:
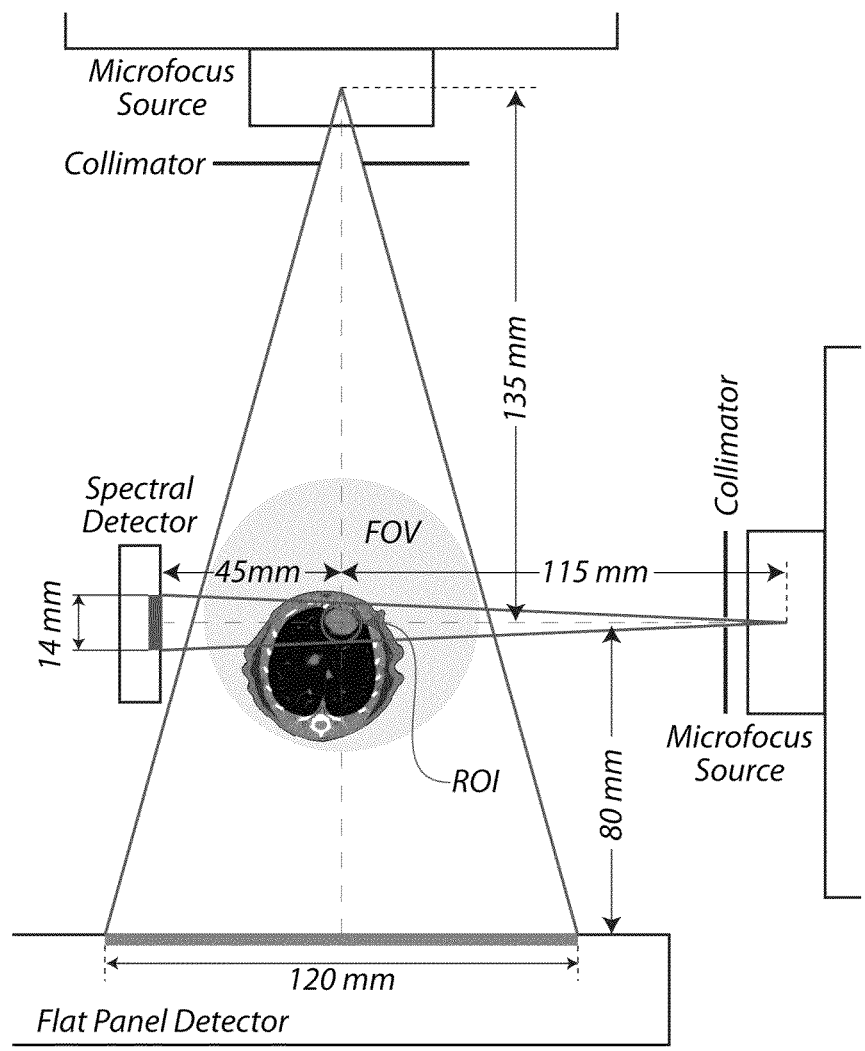
FIG. 12 is a two-dimensional sketch of the hybrid true-color interior micro-CT.

[Design Rationale]. While conventional gray-scale micro-CT still serves many users, spectral true-color micro-CT is often needed in selected ROIs. As shown in FIG. 12, embodiments of the invention combine conventional micro-CT, spectral detection and interior tomography into a hybrid true-color micro-CT system consisting of a wide-beam gray-scale imaging chain and a narrow-beam true-color imaging chain on a rotating slip ring. Somehow, this architecture is similar to a Siemens dual-source scanner (which use different x-ray tube energies and photon integrating detectors) but the unique features of this design include the ultra-fine spectral detector and exact local reconstruction. The hybrid system is capable of being operably configured to comprise a 90 mm global field of view (FOV) and a 10 mm interior ROI for gray-scale and true-color imaging, respectively. Other design features can include 50 μm spatial resolution, 20 HU noise deviation, 8 spectral channels, and up to ¼ rotation per second. This design is also a framework for extension towards multi-source interior true-color micro-CT for ultra-fast data acquisition (Wang, G., H. Yu, et al. 2009), when spectral detectors become cost-effective in the future.

Data Acquisition. The two x-ray tubes are identical from Hamamatsu (L8121-03), allowing the K-edge imaging (80.7 keV) with gold nano-particles. They can be continuously operated in one of three focal spot sizes 7, 20 and 50 μm at up to 150 kV and 500 μA. The gray-scale x-ray detector is a flat panel from Hamamatsu (C7942CA-22) for a 120×120 mm$^2$ sensitive area with pixel size 50×50 μm$^2$. The spectrally-resolving photon-counting x-ray detector is Medipix3 with a readout logic supporting 8 energy thresholds. The data acquisition subsystem adjustment and calibration steps are well known for conventional micro-CT. The spectral data calibration can be performed using pixel gain correction (flat field correction) with a flux x-ray beam (up to 90% of the detector dynamic range), bad-pixel filing with bilinear interpolation, and energy calibration with fluorescence photons from molybdenum (17.5 keV) and gadolinium (43.0 keV) foils generated by an x-ray tube, as well as gamma-rays from isotopes such as a 241 Am source (59.5 keV). Other spectral detection specific artifacts, such as charge sharing, can be suppressed as well. Then, digital preprocessing can be applied, including nonlinear de-noising and de-striping, to produce sinograms for image reconstruction.

Figure 13:
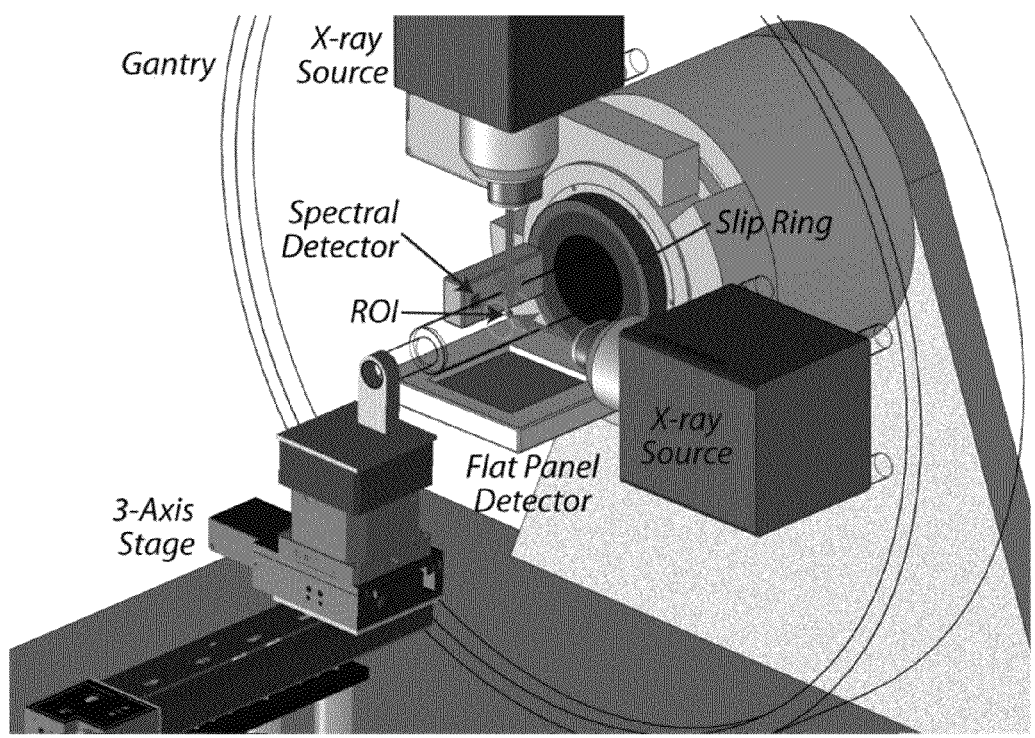
FIG. 13 is a 3-D rendering of the hybrid true-color interior micro-CT.

System integration. As shown in FIG. 13, a slip ring can be used to integrate the two imaging chains for continuous scanning to cover a whole mouse with a helical scan, perform perfusion studies over an extended period, and so on. Two key parameters of embodiments of slip rings according to the invention are an internal diameter of 90 mm and maximum data rate of 300 MB/s. A high precision 3D positioning system can be customized to translate the animal bed within the gantry with a capability to center an ROI in a mouse at the iso-center of the scanning plane for interior tomography. A small-animal monitoring unit (1025L and Signal Breakout Module, SA Instruments) can be used to track the respiration movement and record ECG signals. The physiological waveforms and projection data can also be synchronized. System software with a user friendly interface can employ, for example LabVIEW language. The image reconstruction software can be implemented in C++ and integrated into the hybrid system.

Performance Characterization. Imaging performance can be validated with a customized commercial micro-CT phantom—vmCT 610 Shelley Medical Imaging Technologies, Ontario, Canada). This phantom can include a resolution coil plate, a slanted edge plate, a geometric accuracy plate, a CT number plate, and a uniformity and noise plate (Du, Umoh et al. 2007). Contrast agents such as iodine gold nano-particles with precise concentration and spectral response can be filled into line pairs on spectral imaging plates to test true-color interior tomography including K-edge imaging. Ion-exchange resin beads (150-300 μm diameter, Spectrum Chromatography, Houston, Tex.) can be used to quantify co-registration between the global and interior micro-CT scans. X-ray spectra and radiation dose can be measured using standard devices. Additionally, the major quality and dose indexes can be analyzed to compare different imaging protocols and characterize the hybrid micro-CT system performance.

Alternative Strategies. In some applications, it is recognized that the fixed 10 mm ROI size of the above-described system might be restrictive in practice. If this becomes an issue in preclinical applications, either interior scans can be performed multiple times or two Medipix detectors can be used to enlarge the size of an ROI. Another technique to increase the ROI size is to perform spectral interior reconstruction outside the ROI from both interior spectral data and global gray-scale data, which is known to be unique (Wang, Yu et al. 2008; Ye, Yu et al. 2008) and should be stabilized with the transversely complete gray-scale limited-angle, half-scan or full-scan data. This color-diffusing interior tomography mode is yet another innovative feature of embodiments of the invention.

Spectral Interior Reconstruction. While the inventor's interior tomography (IT) approach is theoretically rigorous and has produced excellent results, there remain two challenges for spectral micro-CT. First, the current interior tomography techniques may generate poor results when data noise is high, which happens to be the case of true-color micro-CT imaging at a high speed (photon limited). (See, e.g., Chan, Esedoglu et al. 2006; and Quinto, Ozan et al. 2010). Second, interior tomography typically requires more computational overhead, which is a bottleneck for its wide-spread preclinical applications. Ironically and interestingly, the less projection data used, the more computational resources needed for accurate image reconstruction. Theoretically exact interior reconstruction demands two orders of magnitude more time than the conventional FBP method, and must be accelerated for routine use.

With the inventive spectral or true-color interior micro-CT architecture shown in FIG. 13, there is provided a conventional scan over the whole FOV and spectral interior projection data through one or more ROIs. It is underlined that color-blinded global data (typically, an entire gray-scale image) is powerful prior knowledge for color interior tomography, which is the key to stabilize color interior reconstruction from highly noisy truncated spectral data. From a computational performance perspective, fast interior tomography algorithms using a state-of-the-art accelerated soft-thresholding technique have been developed (Donoho 1995; Daubechies, Defrise et al. 2004; Daubechies, Fornasier et al. 2008). This type of technique can be adapted for color interior tomography, and be further accelerated with GPU and cloud-computing techniques.

Integrated Reconstruction. The color interior problem defined is to achieve a theoretically exact reconstruction of an ROI from spectral projection data only through the ROI guided by transversely complete global data such as an entire gray-scale image (which is a function of spectrally dependent linear attenuation coefficients and depends on the beam hardening correction approach (in an extreme case, a weighted sum of these spectrally dependent coefficients)). Color interior tomography can be performed much more robustly aided by such global gray-scale information than current interior tomography algorithms in the case of highly noisy truncated spectral data. In this context, ambiguity functions associated with interior reconstruction are strongly constrained by the global gray-scale data, and can be steered to zero using an appropriate computational scheme under practical conditions. First, a common positive constant guess and an integrated SART formulation (Wang and Jiang 2004) can be used to establish the uniqueness, if possible. Then, the formulation with the TV or higher-order TV minimization in an alternating fashion can be enhanced (Wang, Yang et al. 2008; Yu and Wang 2009). Also, it is possible to introduce a correlation maximization criterion such that ambiguity functions are further regularized to vanish. Since the uniqueness of interior tomography was already proved in the single-channel case (Ye, Y., H. Yu, et al. (2008a)), the aforementioned construction of the color interior tomography methodology should not only give the unique solution but also perform very stably under all the available constraints.

Computational Acceleration. The color interior tomography algorithms can be operably configured to be optimized in a fast iterative shrinkage-thresholding algorithmic (ISTA) framework (Beck and Teboulle 2009). Such a scheme is ideal for solving large-scale linear inverse problems with a fastest global convergence rate theoretically and practically proven. Initial promising numerical results for image deblurring demonstrate that this much-improved ISTA approach is faster than ISTA by several orders of magnitude. In addition to algorithmic optimization, high-performance computing techniques can be used as well to improve the color interior reconstruction speed, such as a graphic processor unit (GPU) based computation. Furthermore, the use of the computing cloud is a promising opportunity to add value to the color interior reconstruction software. The computing cloud provides on-demand shared resources and software to users over the Internet. One such provider, Amazon Elastic Computing Cloud (Amazon EC2), provides high flexibility and cost-effectiveness (Evangelinos and Hill 2008). Cloud-based color interior tomography software can be incorporated into systems of the invention. Systems operably configured to deliver a target time for an entire color micro-CT study of well under one hour are highly desirable. Additionally, a user friendly interface can be incorporated as well on the internet to serve the community and facilitate technology transfer.

Feature Extraction. Feature extraction is an important task since spectral micro-CT offers a tremendous volume of information (up to 8 channels). It is well known that feature extraction can either be for representation or classification, being distinct yet related for visualization and analysis. In the current spectral CT literature, principal component analysis (Fukunaga 1990) has been used to transform spectral information into eigen-channels. A subset of eigen-channels associated with larger eigen-values is generally used to minimize the least square error from the original multi-spectral micro-CT images. Principal component analysis can be used in particular applications, however, extracting features using modern statistical methods (Fukunaga 1990) for tissue characterization can also be employed. From training datasets, within-class, between-class, and mixture scatter matrices and the class separability (Fukunaga 1990) can be computed. A within-class scatter matrix describes the scatter of samples around their mean. A between-class scatter matrix represents the scatter of individual class means around the mixture mean. The mixture scatter matrix is the covariance matrix of all samples regardless of their class assignments. The heuristically motivated and theoretically justified class separability measures can be defined in terms of these matrices. Such a measure is larger when the between-class scatter is larger or the within-class scatter is smaller. The most popular separability measures is $/_1 = tr(S_2^{-1} S_1)$, where $S_1$ and $S_2$ are appropriate scatter matrices allowing multiple valid combinations (Fukunaga 1990). Since it is impractical to discuss nonlinear transformations, the focus can be on linear transformations. A linear transformation A from an 8-channel spectral micro-CT reconstruction to an m-dimensional form (m<8) can be uniquely determined by minimizing the corresponding class separability functional, whose column vectors are linearly independent but do not need to be orthonormal. The feature extraction approach should effectively reveal spectral differences characteristic of individual tissue types.

Alternative Strategy. Issues that may surface in some applications include that the color interior tomography approach described above might need further improvement since spectral micro-CT is photon-limited when both data rate and channel number are sufficiently large. In this case, a likelihood-maximization-based interior tomography approach can be used.

For example, let us assume that a single-channel micro-CT scan measures a set of projection data represented as a 1D vector Y with elements $Y_i^{meas}$, i=1, ..., $N_Y$, from an underlying image F. Then, each measurement is a realization of a random variable and can be reduced under the practical conditions to $$Y_i^{meas} \sim \text{Poisson}\left\{I_i \exp\left[-\sum_{j=1}^{N_p} a_{ij}\mu_j\right] + r_i\right\}$$

where an object consists of $N_p$ pixels with attenuation coefficients $\mu = [\mu_1, \mu_2, \ldots, \mu_N]^2$, $a_{ij}$ denotes weights, and $r_i$ a known constant for measurement noise (La Riviere, Bian et al. 2006). In this project, if necessary we can maximize $\Phi_L(F; Y) = L(F,Y) - \beta R(F)$ where L(F,Y) is the composite Poisson likelihood functional for all the spectral channels and R(F) implements all the constraints to improve the image quality of color interior micro-CT further using the computing techniques similar to those recently reported in (Defrise, Vanhove et al. 2010; Liu, Defrise et al. 2010).

Preclinical Applications. Three types of complementary mouse studies are included. The first study on xenograft breast cancer can be used to demonstrate the potential of spectral CT for tumor imaging. The second study on environmentally-modulated fetal programming can be used to establish the capability of spectral CT for vasculature imaging. The third study on fatty liver disease can be used primarily for cross-validation of the inventive hybrid color micro-CT system and the state-of-the-art MARS color micro-CT system. Synergistically, these studies push the imaging performance envelope in terms of spatial, contrast and energy resolution at the minimum radiation dose, and would generally accelerate biomedical applications of spectral CT techniques.

Color Micro-CT of Xenograft Caner. Color micro-CT can be used to exhibit higher contrast resolution of tumors in mice bearing breast cancer cells compared to conventional micro-CT. Breast cancer is the second leading cause of cancer death in women in the USA (American Cancer Society, 2010). Detection at an early stage is critical for much better prognosis of breast cancer patients. X-ray imaging (mammography) is a primary mode for breast cancer screening and diagnosis but the contrast resolution is rather limited and significantly compromises sensitivity and specificity, demanding major improvement with minimal radiation dose. As discussed above, spectral x-ray imaging aided by gold nano-particles offers an exciting opportunity in this context.

An animal tumor model can be employed to determine whether the proposed true-color micro-CT would significantly enhance imaging capability over the conventional gray-scale micro-CT. Eighteen 4- to 6-week-old female nude mice (Nu/Nu Nude Mouse, Crl:NU-Foxn1$^{nu}$) can be purchased from Charles River Laboratories (Wilmington, Mass.). Animals can be maintained under environmentally controlled conditions and subjected to a 12 h light/dark cycle with food and water ad libitum. Animal quantities are justified by power calculation and sample size analysis using the statistical software SigmaStat 3.5 (See the Vertebrate Animals section for the details). Human breast cancer cells, MDA-MB-468, can be obtained from ATCC and cultured in Leibovitz's L-15 medium supplemented with 10% fetal bovine serum, 100 U/ml penicillin, and 100 µg/ml streptomycin. The mouse model of MDA-MB-468 breast cancer can be established as described previously (Wu, Qiu et al. 2008).

Briefly, 100 µA of phosphate buffered saline (PBS) containing MDA-MB-468 cells ($5 \times 10^6$ cells) can be injected into the mammary fat pad of each mouse. On day 10 of post-tumor cell implantation, when the MDA-MB-468 tumors reach 70-110 mm$^3$ in volume, 100 µA of PBS containing gold nano-particles (100 µg/ml) (AuroVist™ Gold Nano-particle X-ray Contrast Agent; Nanoprobes, Yaphank, NY) can be injected into mice through a tail vein (Hainfeld, Slatkin et al. 2006). 2 min after injection of the contrast agent, mice can be randomly divided into two experimental groups (n=9) and either conventional micro-CT or true-color interior micro-CT can be used to image angiogenic and hypervascularized regions under various imaging protocols of different radiation and contrast dose levels. The same procedure can be conducted twice per week until the tumor reaches a desired volume, such as a volume of 1,500 mm$^3$. Tumor size can be measured using Vernier calipers, and their volumes can be calculated as $0.5 \times L \times W^2$, where L is along the longest axis and W is along the orthogonal direction.

Color Micro-CT of Vascular Biomarkers. Fetal growth and birth outcome are directly related to genetics, maternal health, and environmental factors, such as prenatal nutrition. Poor prenatal environment causes fetal growth restriction (FGR) and is believed to elevate lifelong risk of chronic diseases. The quality of the placenta is hypothesized to reflect the prenatal environment, FGR, and susceptibility to adult-onset disease in offspring. Recent studies revealed that the viability of syncitiocapillary membranes in the placental terminal villi is the most reliable predictor of FGR (Aviram, T et al. 2010); reduced placental vascularization and underperfusion cause fetal asphyxia, reduced fetal nutrients, and ischemia-reperfusion injury, which are referred to as "fetal programming". Imaging placental vasculopathy would provide a window of opportunity during which maternal environment could be corrected to improve birth outcome and reduce lifelong risk of metabolic diseases. Pilot studies in Dr. Prater's laboratory suggest placental vascular biomarkers (vessel necrosis and inflammation) following maternal consumption of high fat diet (HFD) (Prater, Laudermilch et al. 2008). Follow-up studies using CD31 immunofluorescent confocal microscopic imaging of vascular labyrinthine placenta showed endothelial targeting which likely contributed to FGR (Liang, DeCourcy et al. 2010). These methods are expensive, time-consuming, and are limited to 2D analysis.

Recently, gold nano-particles were used to visualize tumor-related microangiographic (<8 µm) changes (Chien, Wang et al. 2010). Similarly, gold nano-particles can be used here to visualize impairment of placental microvasculature following HFD. Gold nano-particles of <30 nm in diameter circulate through and remain in murine vasculature over >24 hr, without penetrating cell membranes (Sadauskas, Wallin et al. 2007). These particles readily enter placental vessels, and do not appreciably cross placental barriers into fetus, thus serving as a safe and superior method to study effects of prenatal environment on placental vasculature (Myllynen, Loughran et al. 2008; Kojima, Umeda et al. 2010).

Spectral micro-CT studies can be conducted on late gestation murine placental vasculature following tail vein infusion of gold nano-particles. Seventy 6-week old female and ten 6-week old male C57BL/6J mice can be obtained from Jackson Laboratories (Bar Harbor, Me.), acclimated 1 wk at the VMRCVM Nonclient Animal Facility, then arbitrarily divided into two feeding groups (control diet) or (HFD) for one month, n=5/group. Females can be bred overnight, and checked at 12 and 24 hr for vaginal plugs, indicating breeding. Male mice can be removed, and females can remain on their diets through gestation. On gestation day 18 (one day prior to parturition), monodispersed 1.9 or 15 nm particles (AuroVist™) can be infused into anesthetized dams via tail vein injection at a rate of no less than 5 min per injection in a modified protocol by (Sadauskas, Wallin et al. 2007). Micro-CT images of placenta (50 µm resolution) can be obtained immediately following euthanasia via carbon dioxide asphyxiation at 6, 12, and 24 hr post injection, and reconstructed images can be evaluated for micro-structural properties in terminal villi, and independently verified using histological and statistical analysis.

Based on the literature and preliminary studies, 1.9 and 15 nm gold nano-particles are capable of readily, rapidly, and evenly being distributed through placental vasculature, and can remain stable within the vasculature for >24 hr. Because spectral micro-CT can further increase contrast resolution in terms of spectral characteristics including L- and K-edges, a target spatial resolution of 50 µm can be used to enable exquisite reconstruction of placental vasculature, and provide novel information linking gestational HFD to poor placental vasculature and elevated risk of poor birth outcome and lifelong impaired health.

Should rate of placental saturation with nano-particles vary outside initial expectation, earlier/later imaging time points can be added. Additionally, Gold nano-particles may be specifically labeled with endothelial antigen (CD31) or trophoblast specific antigen (MA21) for spectral micro-CT imaging.

Color Micro-CT of Fatty Liver Disease. Metabolic syndrome (MetS) including non-alcoholic fatty liver disease has significant public health implications because it is associated with a two-fold increased risk of coronary heart disease (CHD) (Alexander 2003), a three- to four-fold increased risk of mortality due to CHD (Jones, A W. et al. 2000) and a six-fold increased risk of type 2 diabetes (Laaksonen, Lakka et al. 2002). MetS can be imaged with CT, showing low density fat regions within the liver (Longo, Patel et al. 2005). A comparative study of fatty-liver content measurement was recently performed with ultrasound, CT and MRI (Qayyum, Chen et al. 2009). Although well-established for severe cases, the ability to distinguish fatty-liver at moderate levels has been controversial. Unenhanced CT is limited by the presence of iron and glycogen in the liver, and improved to some degree with dual-energy CT (Graser, Johnson et al. 2009). Using the spectral CT method (Rodgers 1996; Thomaz, Gillies et al. 2004)I, it is clinically desirable, and technically feasible, to image liver components of pathological interest much more sensitively and specifically.

A mouse model of MetS can be studied and a colony of hybrid ArKO/ApoE$^{-/-}$ mice is available to assess a range of imaging modalities, including spectral micro-CT. A particular emphasis is on accumulation of abnormal abdominal fat around the liver and kidneys (visceral adiposity) as well as expansion of all major subcutaneous fat deposits. Specifically, 10 fixed euthanized mice can be studied. The mice can be euthanized and fixed in a standard resin (CraftSmart liquid gloss, CraftSmart Australia, Glayton North, Australia) within 25 mm internal diameter PMMA (polymethyl methacrylate) tubing. Subcutaneous and intra-organ fat deposits and organ masses can be quantified. Fat/water ratios in regions of adiposity can be calculated (Zhang, Tengowski et al. 2004), in addition to Adipocyte volume (Jones, A W. et al. 2000). Excised infrarenal fat pads and the whole liver can be weighed, stained with haematoxylin and eosin (H&E), and analyzed for comparison.

Datasets collected on different scanners from the same fixed mice can be compared to validate the inventive color interior tomography approach and architecture. Second, on the same imaging platform (Medipix detectors) and the same mouse model, a better understanding of spectral micro-CT performance for preclinical research with an emphasis on feature extraction via advanced dimensionality reduction techniques such as the principle component analysis can be achieved.

Akolekar, D. B., G. Foran, et al. (2004). "X-ray absorption spectroscopic studies on gold nanoparticles in mesoporous and microporous materials." J Syn. Rad. 11(Pt 3): 284-290.

Alexander, C. M. (2003). "The coming of age of the metabolic syndrome." Diabetes Care 26(11): 3180-3181.

Anderson, N. G., A. P. Butler, et al. (2010). "Spectroscopic (multi-energy) CT distinguishes iodine and barium contrast material in MICE." Eur Radiol.

Aviram, R., B. S. T, et al. (2010). "Placental aetiologies of foetal growth restriction: clinical and pathological differences." Early Hum Dev 86(1): 59-63.

Beck, A. and M. Teboulle (2009). "A Fast Iterative Shrinkage-Thresholding Algorithm for Linear Inverse Problems." Siam Journal on Imaging Sciences 2(1): 183-202.

Cahn, R. N., B. Cederstrom, et al. (1999). "Detective quantum efficiency dependence on x-ray energy weighting in mammography." Med Phys 26(12): 2680-2683.

Campbell, M., E. H. M. Heijne, et al. (1998). "A readout chip for a 64×64 pixel matrix with 15-bit single Photon Counting." IEEE Trans. on Nuclear Science 45(3): 751-753.

Candes, E. J., J. Romberg, et al. (2006). "Robust uncertainty principles: Exact signal reconstruction from highly incomplete frequency information." IEEETransactions on Information Theory 52(2): 489-509.

Chan, T., S. Esedoglu, et al. (2006). "Recent developments in total variation image restoration." Handbook of Mathematical Models in Computer Vision, eds Paragios N, Chen Y, Faugeras O (Springer-Verlag, Berlin): 3.

Chien, C. C., C. H. Wang, et al. (2010). "Synchrotron microangiography studies of angiogenesis in mice with microemulsions and gold nanoparticles." Anal Bioanal Chem.

Dammer, J., P. M. Frallicciardi, et al. (2009). "Real-time in-vivo mu-imaging with Medipix2." Nuclear Instruments & Methods in Physics Research Section a-Accelerators Spectrometers Detectors and Associated Equipment 607(1): 205-207.

Daubechies, I., M. Defrise, et alt. (2004). "An iterative thresholding algorithm for linear inverse problems with a sparsity constraint." Communications on Pure and Applied Mathematics 57(11): 1413-1457.

Daubechies, I., M. Fornasier, et al. (2008). "Accelerated Projected Gradient Method for Linear Inverse Problems with Sparsity Constraints." Journal of Fourier Analysis and Applications 14(5-6): 764-792.

Defrise, M., C. Vanhove, et al. (2010). "Iterative reconstruction in micro-CT." The First International Conference on Image Formation, Salt Lake City, Utah.

Donoho, D. L. (1995). "De-noising by soft-thresholding." IEEE Trans. Inform. Theory 41: 613-627.

Donoho, D. L. (2006). "Compressed sensing." IEEE Transactions on Information Theory 52(4): 1289-1306.

Du, L. Y., J. Umoh, et al. (2007). "A quality assurance phantom for the performance evaluation of volumetric micro-CT systems." Phys Med Biol 52(23): 7087-7108.

Evangelinos, C. and C. N. Hill (2008). "Cloud Computing for parallel Scientific HPC Applications: Feasibility of running Coupled Atmosphere-Ocean Climate Models on Amazon's EC2." Ratio 2.

Faridani, A., D. V. Finch, et al. (1997). "Local tomography II." SIAM J. Appl. Math. 57(4): 1095-1127.

Faridani, A., E. L. Ritman, et al. (1992). "Local tomography." SIAM J. Appl. Math. 52: 459-484.

Firsching, M., A. P. Butler, et al. (2009). "Contrast agent recognition in small animal CT using the Medipix2 detector." Nuclear Instruments & Methods in Physics Research Section a-Accelerators Spectrometers Detectors and Associated Equipment 607(1): 179-182.

Frallicciardi, P. M., J. Jakubek, et al. (2009). "Comparison of single-photon counting and charge-integrating detectors for X-ray high-resolution imaging of small biological objects." Nuclear Instruments & Methods in Physics Research Section a-Accelerators Spectrometers Detectors and Associated Equipment 607(1): 221-222.

Fukunaga, K. (1990). Introduction to statistical pattern recognition

Giersch, J., D. Niederlohner, et al. (2004). "The influence of energy weighting on X-ray imaging quality." Nuclear Instruments & Methods in Physics Research Section a-Accelerators Spectrometers Detectors and Associated Equipment 531(1-2): 68-74.

Graser, A., T. R. Johnson, et al. (2009). "Dual energy CT: preliminary observations and potential clinical applications in the abdomen." Eur Radiol 19(1): 13-23.

Greiffenberg, D., M. Fiederle, et al. (2009). "Detection efficiency of ATLAS-MPX detectors with respect to neutrons." Nuclear Instruments & Methods in Physics Research Section a-Accelerators Spectrometers Detectors and Associated Equipment 607(1): 38-40.

Hainfeld, J. F., D. N. Slatkin, et al. (2006). "Gold nanoparticles: a new X-ray contrast agent." Br J Radiol 79(939): 248-253.

Han, W., H. Yu, et al. (2009). "A total variation minimization theorem for compressed sensing based tomography." Phys Med Biol: under review.

Jakubek, J. (2009). "Semiconductor Pixel detectors and their applications in life sciences." Journal of Instrumentation 4: -.

Jakubek, J., C. Granja, et al. (2007). "Phase contrast enhanced high resolution X-ray imaging and tomography of soft tissue." Nuclear Instr. & Methods in Physics Research Section a-Accelerators Spectrometers Detectors and Associated Equipment 571(1-2): 69-72.

Jones, M., T. A W., et al. (2000). "Aromatase-deficient (ArKO) mice have a phenotype of increased adiposity." Proc Natl Acad Sci USA 97(23).

Kojima, C., Y. Umeda, et al. (2010). "X-ray computed tomography contrast agents prepared by seeded growth of gold nanoparticles in PEGylated dendrimer." Nanotechnology 21(24): 245104.

Kudo, H., M. Courdurie, et al. (2007). Tiny a priori knowledge solves the interior problem. 2007 IEEE Nuclear Science Symposium Conference 4068-4075.

Kudo, H., M. Courdurier, et al. (2008). "Tiny a priori knowledge solves the interior problem in computed tomography." Phys. Med. Biol. 53(9): 2207-2231.

La Riviere, P. J., J. G. Bian, et al. (2006). "Penalized-likelihood sinogram restoration for computed tomography." IEEE Trans. on Medical Imaging 25(8): 1022-1036.

Laaksonen, D. E., H. M. Lakka, et al. (2002). "Metabolic syndrome and development of diabetes mellitus: application and validation of recently suggested definitions of the metabolic syndrome in a prospective cohort study." Am J Epidemiol 156(11): 1070-1077.

Liang, C., K. DeCourcy, et al. (2010). "High-saturated-fat diet induces gestational diabetes and placental vasculopathy in C57BL/6 mice." Metabolism 59(7): 943-950.

Liu, X., M. Defrise, et al. (2010). "Total variation regulated iterative algorithms for microCT." The First International Conference on Image Formation, Salt Lake City, Utah.

Llopart, X., M. Campbell, et al. (2002). "Medipix2: a 64-k pixel readout chip with 55 mu m square elements working in single photon counting mode." Ieee Transactions on Nuclear Science 49(5): 2279-2283.

Longo, C. R., V. I. Patel, et al. (2005). "A20 protects mice from lethal radical hepatectomy by promoting hepatocyte proliferation via a p21 waf1-dependent mechanism." Hepatology 42(1): 156-164.

Myllynen, P. K., M. J. Loughran, et al. (2008). "Kinetics of gold nanoparticles in the human placenta." Reprod Toxicol 26(2): 130-137.

Natterer, F. (2001). The Mathematics of Computerized Tomography. Philadelphia, Society for Industrial and Applied Mathematics.

Prater, M. R., C. L. Laudermilch, et al. (2008). "Placental oxidative stress alters expression of murine osteogenic genes and impairs fetal skeletal formation." Placenta 29(9): 802-808.

Qayyum, A., D. M. Chen, et al. (2009). "Evaluation of diffuse liver steatosis by ultrasound, computed tomography, and magnetic resonance imaging: which modality is best?" Clin Imaging 33(2): 110-115.

Quinto, E. T. (2007). "Local algorithms in exterior tomography." Journal of Computational and Applied Mathematics 199(1): 141-148.

Quinto, E. T. and O. Oktem (2007). "Local tomography in electron microscopy." Siam Journal on Applied Mathematics 68(5): 1282-1303.

Quinto, E. T., O. Ozan, et al. (2010). "Reply to Wang and Yu: Both electron lambda tomography and interior tomography have their uses." Proceedings of the National Academy of Sciences of the United States of America 107(22): E94-E95.

Ramm, A. G. and A. I. Katsevich (1996). The Randon Transform and Local Tomography. Boca Raton, CRC Press.

Rodgers, C. (1996). "Information content and optimisation of high spectral resolution measurements." In Proc. SPIE 2830.

Rudin, L. I., S. Osher, et al. (1992). "Nonlinear Total Variation Based Noise Removal Algorithms." Physica D 60(1-4): 259-268.

Sadauskas, E., H. Wallin, et al. (2007). "Kupffer cells are central in the removal of nanoparticles from the organism." Part Fibre Toxicol 4: 10.

Schlomka, J. P., E. Roessl, et al. (2008). "Experimental feasibility of multi-energy photon-counting K-edge imaging in pre-clinical computed tomography." Physics in Medicine and Biology 53(15): 4031-4047.

Shikhaliev, P. M. (2005). "Beam hardening artefacts in computed tomography with photon counting, charge integrating and energy weighting detectors: a simulation study." Physics in Medicine and Biology 50(24): 5813-5827.

Sorgenfrei, R., D. Greiffenberg, et al. (2008). "Growth of thick films CdTe from the vapor phase." Journal of Crystal Growth 310(7-9): 2062-2066.

Swank, R. K. (1973). "Calculation of modulation transfer functions of x-ray fluorescent screens." Appl Opt 12(8): 1865-1870.

Thomaz, C. E., D. F. Gillies, et al. (2004). "A new covariance estimate for Bayesian classifiers in biometric recognition." Ieee Transactions on Circuits and Systems for Video Technology 14(2): 214-223.

Wang, G. and M. Jiang (2004). "Ordered-Subset Simultaneous Algebraic Reconstruction Techniques (OS-SART)." J. of X-ray Science and Technology 12(3): 169-177.

Wang, G. and H. Yu (2008). Methods and Systems for Exact Local CT Based on Compressive Sampling. See, e.g., U.S. Provisional Application No. 61/169,577 and applications claiming priority to this application.

Wang, G. and H. Yu (2010). "Can interior tomography outperform lambda tomography?" Proc Natl Acad Sci USA 107(22): E92-93, author reply E94-95.

Wang, G., H. Yu, et al. (2008). "Interior Tomography: Practical Applications." Biomedical Mathematics Promising Directions in Imaging, Therapy Planning, and Inverse Problems Chapter 26: 13.

Wang, G., H. Yu, et al. (2009). "A scheme for multisource interior tomography." Med Phys 36(8): 3575-3581.

Wang, Y. L., J. F. Yang, et al. (2008). "A New Alternating Minimization Algorithm for Total Variation Image Reconstruction." Siam J. on Imaging Sci. 1(3): 248-272.

Wang, Z., L. Wu, et al. (2010). "Size-tunable synthesis of monodisperse water-soluble gold nanoparticles with high X-ray attenuation." Chemistry 16(5): 1459-1463.

Wu, G. K., X. L. Qiu, et al. (2008). "Small Molecule Targeting the Hec1/Nek2 Mitotic Pathway Suppresses Tumor Cell Growth in Culture and in Animal." Cancer Research 68(20): 8393-8399.

Xu, C., G. A. Tung, et al. (2008). "Size and Concentration Effect of Gold Nanoparticles on X-ray Attenuation As Measured on Computed Tomography." Chem Mater 20(13): 4167-4169.

Ye, Y., H. Yu, et al. (2007). "Exact Interior Reconstruction with Cone-beam CT." International Journal of Biomedical Imaging 2007: Article ID: 10693, 10695 pages.

Ye, Y., H. Yu, et al. (2008). "Interior Tomography: Mathematical Analysis." Biomedical Mathematics Promising Directions in Imaging, Therapy Planning, and Inverse Problems Chapter: 19.

Ye, Y., H. Yu, et al. (2007). "A general local reconstruction approach based on a truncated Hilbert transform." International Journal of Biomedical Imaging 2007: Article ID: 63634, 63638 pages.

Ye, Y., H. Y. Yu, et al. (2008). "Exact interior reconstruction from truncated limited-angle projection data." International Journal of Biomedical Imaging 2008: Article ID: 427989, 427986 Pages.

Yu, H. and G. Wang (2009). "Compressed sensing based Interior tomography." Phys Med Biol 54(9): 2791-2805.

Yu, H., J. Yang, et al. (2009). "Further analysis on compressed sensing based interior tomography." Phys Med Biol 54(18): N425-N432.

Yu, H., Y. Ye, et al. (2008). "Local Reconstruction Using the Truncated Hilbert Transform via Singular Value Decomposition." J. of X-Ray Sci. and Tech. 16(4): 243-251.

Yu, H. Y., Y. C. Wei, et al. (2007). "Lambda tomography with discontinuous scanning trajectories." Physics In Medicine And Biology 52(14): 4331-4344.

Zhang, X. W., M. Tengowski, et al. (2004). "Measurement of fat/water ratios in rat liver using 3D three-point dixon MRI." Magnetic Resonance in Medicine 51(4): 697-702.

Zwerger, S., M. H. Abu-Id, et al. (2007). "[Long-term results of fittig subperiosteal implants: report of twelve patient cases]." Mund Kiefer Gesich. 11(6): 359-362.

III. Sparsity-Regularized Computational Optical Biopsy (SCOB) The inventors additionally provide methods, systems, and devices using a sparsity-regularized computational optical biopsy (SCOB) approach to locate and quantify bioluminescent probes regardless of source depth. More particularly, using fiber-optic technology a small number of internal photon fluence rate values can be measured minimally invasively. Then, the bioluminescent source distribution can be accurately and stably reconstructed by a stochastic optimization method using the source sparsity as a constraint.

As background, very generally, optical molecular imaging has its unique merits in pre-clinical imaging [1, 2B]. Tomographic techniques, such as fluorescent molecular tomography (FMT) [3B, 4B] and bioluminescence tomography (BLT) [5B, 6B], were developed to retrieve the depth and characterized the strength of the molecular probes. However, fluorescent and bioluminescent photons penetrate only about 3 cm in biological tissue; therefore, is limited by its detection depth and currently only found applications in small animal studies.

In 2003, the inventors devised a computational optical biopsy (COB) technology [7B, 8B] to measure and calculate fluorescent and bioluminescent source parameters in a local in vivo environment. Spatially and spectrally resolved data collected using fiber-optic detectors along one or multiple trajectories are processed for estimation of the light-emitting source parameters of interest. Minimally invasive fiber-optic sensors have been also developed by other groups [9B, 11B]. Such devices can penetrate biological tissues to deliver and collect light and have been used to measure microscopic brain motions in vivo [10B] and perform optical coherence tomography (OCT) [11B]. This type of optical sensing technology presents an effective solution to image bioluminescent or fluorescent probes in large animals and clinical applications. Optical fiber detectors can also be integrated within tissue-engineered scaffolds to perform molecular imaging functionality. The scaffold can be implanted into a living animal with optical fibers extended out of the animal body for continuous information collection; this technique could measure the degree of cell and tissue growth and void formation without removing the scaffold from the animal. However, the optical fluence rate signals acquired by this type of device are severely under-sampled, and thus present a challenging task to the signal reconstruction.

The bioluminescent source distribution, which is often sparse, can be used to regularize this highly ill-posed problem. Combining fiber-optic detection and sparsity regularization, the inventors provide a novel imaging approach to reconstruct the bioluminescent source distribution in any designated FOV using a small number of measurements; further referred to as sparsity-regularized computational optical biopsy (SCOB). SCOB alleviates the limitation in detection depth and provides a viable solution for optical molecular imaging in large animals, engineered tissues, and patients.

Radiative transfer equation (RTE) models are used to predict the photon propagation in biological tissues [14B]. Unfortunately, the direct solution to the RTE is complex in 3D. Several approximate solutions to the RTE have been developed, such as diffusion approximation (DA) [15B], spherical harmonics [16B], and phase approximation (PA) [17B]. The diffusion approximation is the most popular because of its sufficient accuracy in optical diffusive media and high computational efficiency. The diffusion equation is [15B]: $-\nabla \cdot (x(r) \nabla \Phi(r)) + \mu_a(r)\Phi(r) = q(r), r \in \Omega$, where $\Phi$ is the photon fluence rate, pa the absorption coefficient, $\kappa$ the diffusion coefficient, q the source distribution, r the position vector. A matched boundary condition can be used and the finite element method (FEM) to solve the diffusion equation [18B, 19B]. The numerical solution to the diffusion equation can be obtained by solving a matrix equation linking the source distribution to the photon fluence rate [19B] as follows: $\Phi = AQ$ where A is the finite element system matrix. It is possible to recover the source distribution in the FOV from a limited number of photon fluence rate measurements. Accordingly, the sampling process can be expressed as [12B]:

$\Phi_m = M\Phi = MAQ = UQ$, where M is the measurement matrix with dimension of m×n. m is the number of measurements, and n is the number of discritized point in the FOV. The measurement matrix is defined with the element at the ith row and the jth column being one if ith measurement is made at jth point in the FOV and being zero otherwise. The reconstruction of the vector Q of n elements from only m measurements (m<<n) is a highly under-determined problem.

Fortunately, many in vivo studies involve small and isolated sources, and these sources can be modeled using points. Using the number of source as a constraint, the problem is converted to: $\min_{(q_1>0, \ldots, q_s>0)} \|UQ - \Phi_m\|$, where Q only includes S positive nonzero values q1, . . . , qs, which represents the power of the point sources, while the remaining components of Q are zeros.

Using a differential evolution optimization technique, the source distribution Q can be recovered.

IV. Photoacoustic Tomography. Photoacoustic tomography (PAT) is a promising imaging technique to differentiate the optical absorption property three-dimensionally. In fluorescence imaging, the absorption and scattering processes greatly limit the penetration depth and reconstruction resolution. First, the excitation light needs to reach the fluorophore location, and then the weak emission light needs to escape the specimen. Even the emission light can be externally detected, the diffuse nature of the light makes the reconstruction extremely difficult. Instead of detecting the diffusive light, PAT detects the resultant ultrasound signal, which has a much better penetration power than the optical signal, due to the photoacoustic effect. More specifically, in PAT a short-pulse laser illuminates on the surface of the specimen and diffuses into it. In the light propagation process, some of the light is absorbed by the specimen and converted into heat. The increment of temperature will change the volume of the heated region. Since the energy is packed in a very short pulse, the rapid changing of temperature will introduce an ultrasound wave, which can be picked up by an ultrasound transducer and reconstructed by ultrasound imaging techniques. Since many fluorescence probes, such as quantum dots, nano-particles, and fluorescence proteins, have much higher absorption coefficients than the normal tissue, photoacoustic tomography offers a high contrast mechanism for fluorescence imaging.

Photoacoustic imaging was introduced in 1991 by Diebold et al. [101A, 102A]. Then, several groups expanded the idea and applied it in several fields [103A-108A]. A reflection-mode confocal photoacoustic microscopy was presented with better than 100 µm resolution and up to ~3 mm depth in vivo [105A]. In this reflection-mode design, a fiber delivers 532 nm laser pulses (300 mJ per pulse of 6.5 ns width) to a customized optical system, which focuses the laser energy in the specimen. A matching ultrasound transducer overlaps its focal spot on the optical focal spot to suppress the out of focus photoacoustic signal. Typically, the system scans the whole imaging region. Recently, a trans-illumination design was introduced with an x-ray CT style scanning mode [104A]. In this design, the pulsed laser is reformed into a laser line in the specimen, a cylindrical transducer then focuses on the focused laser line to pick up the ultrasound signal. While the specimen is rotated in the chamber, the laser line then scans over a section of the specimen. A filtered back projection algorithm can be used to reconstruct the detected acoustic signal [109A].

V. Photoacoustic BLT. The inventors have developed a bioluminescence tomography system based on photoacoustic tomography. In bioluminescence imaging, biological entities (e.g., tumor cells, genes) are encoded with luciferase enzymes as probes in a mouse body for biomedical research. When the luciferase is combined with the substrate luciferin, oxygen and ATP, a biochemical reaction occurs to transform part of the chemical energy into bioluminescent photons with a wavelength of about 600 nm. In small animal studies, a significant number of bioluminescent photons can escape the attenuating environment, and be detected with a highly sensitive charge-coupled device (CCD) camera. Because the biological tissue does not emit photons and no external light source is required for excitation, the background noise in bioluminescent imaging is very low. Bioluminescence tomography (BLT) can be used to localize and quantify bioluminescent sources in a small living animal. Advancing planar bioluminescent imaging to the tomographic imaging framework, BLT helps detect gene expression, monitor therapies and facilitate drug development, among many other applications.

Photon scattering predominates over absorption in the biological tissue. The photon propagation can be described by the steady-state diffusion equation, $$-\nabla \cdot (D(x)\nabla \Phi(x)) + \mu_a(x)\Phi(x) = S(x)(x \in \Omega) D(x) = (3(\mu_a(x) + (1-g)\mu_s(x)))^{-1}, \quad \text{EQUATION (1-1)}$$

where $\Phi(x)$ represents the photon flux density [Watts/cm$^2$], $S(x)$ the energy density distribution of a light source [Watts/cm$^3$], $\mu_a(x)$ the absorption coefficient [cm$^{-1}$], $\mu_s(x)$ the scattering coefficient [cm$^{-1}$], and g the anisotropy parameter.

BLT is used to reconstruct the bioluminescence source $S(x)$ from the boundary measurement based on the physical model (1B). In Eq. (1-1), the optical parameters $\mu_a(x)$, $\mu_s(x)$ and g are unknown. The optical parameters $\mu_a(x)$, $\mu_s(x)$ and source $S(x)$ cannot be simultaneously reconstructed only from boundary measurement. Accordingly, the inventors have identified a modality fusion imaging methodology that can be used to recover the optical parameters using the photoacoustic imaging modality for a better forward modeling so that BLT reconstruction quality can be improved.

Photoacoustic imaging (PAI) is a promising tool for visualizing light absorbing structures in an optically scattering medium. It can resolve common chromophores with spatial resolution exceeding that of ultrasound. The method relies on detection of ultrasonic waves that are photoacoustically induced following absorption of light by tissue chromophores. The amplitude of the generated broadband ultrasound wave reflects local optical absorption properties. Using photoacoustic tomography (PAT) [1B], the initially generated acoustic pressure as a product between optical absorption distribution $\mu_a(x)$ and local light fluence $\Phi(x)$ can be reconstructed from the recorded acoustic signals. Using an optimization procedure, optical absorption and diffusion coefficients can be obtained from the reconstructed optoacoustic image $P(x) = \mu_a(x)\Phi(x)$ based on diffusion equation (1-1) [2B].

$$(D(x), \mu_a(x)) = \arg\min \|\mu_a(x)\Phi(x) - P(x)\|, \quad \text{EQUATION (1-2)}$$

which can be enhanced using traditional diffusion optical tomography (DOT) measurement as well.

In contrast to DOT which represents an ill-posed problem, the optimization procedure (2B) is a well-posed, and can reconstruct optical parameters stably because the known information $P(x)$ is 3D volumetric measurement instead of 2D surface measurement.

Once the optical parameters of a small animal are mapped out using PAT and DOT, we can reconstruct the bioluminescence source distribution from Eq. (1-1) using the compressive sensing method as follows:

$$\begin{cases} \min \|S\|_1 \\ \text{s.t.} \quad \|A\{S\} - \{\Phi_{ex}\}\| \leq \varepsilon \\ S \geq 0 \end{cases} \quad \text{EQUATION (1-3)}$$

where A is a weighting matrix of sources, $\{S\}$ the bioluminescent source distribution, and $\{\Phi_{ex}\}$ the measured photon fluence rate data. Eq. (1-3) is convex programming and can be solved in polynomial time to obtain $\{S\}$.

Note that the diffusion approximation used above is an example. The same problem can be solved using other variants of the radiative transport equation especially the phase-approximation model the inventors recently developed to describe the forward imaging model more accurately.

Hence, our BLT reconstruction process can be improved by PAT and compressive sensing theory and techniques, allowing more reliable and more accurate localization and quantification for bioluminescence sources inside an animal.

REFERENCES (1B) M. Xu and L. V. Wang, "Universal back-projection algorithm for photoacoustic-computed tomography," Phys. Rev. E 71 (1): 016706 (2005).

(2B) Zhen Yuan, Qiang Wang, and Huabei Jiang, "Reconstruction of optical absorption coefficient maps of heterogeneous media by photoacoustic tomography coupled with diffusion equation based regularized Newton method," Opt. Express 15, 18076-18081 (2007).

VI. Deep Tissue Photoacoustic Tomography.

Figure 14:
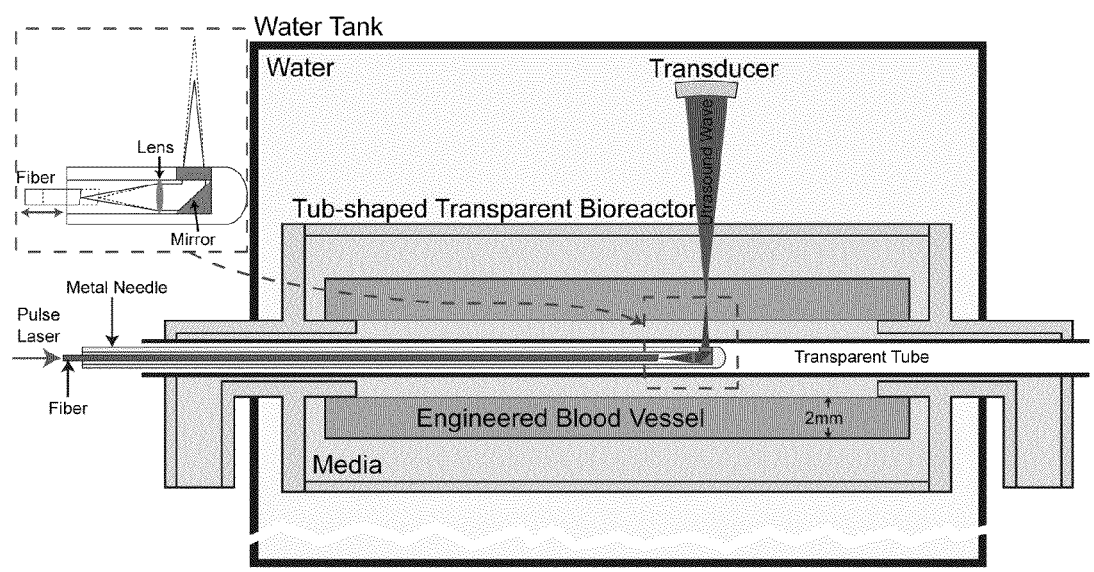
FIG. 14 is a schematic diagram showing the top-level design of the photoacoustic tomography system for molecular imaging of an engineered blood vessel.

PAT for Engineered Blood Vessel. With the deep penetration depth and high 3D resolution capability, photoacoustic tomography is capable of resolving the fluorescence distribution in an engineered tissue environment. The inventors provide a photoacoustic tomography system for engineered blood vessel fluorescence imaging. As shown in FIG. 14, a strong needle, which houses an optic fiber, a lens, and a mirror, delivers a sequence of laser pulses into the wall of an engineered blood vessel. A focused transducer can be configured such that the focused point of the transducer is overlapped with the focused laser spot. The needle and the transducer are steadily mounted on 3D position and rotation stages. As shown in the magnified view of the needle in FIG. 14, the laser focal spot can target different depths of the vessel wall by adjusting the distance between the optical fiber tip and the lens within the needle. While the laser focal spot focuses at a particular depth, the transducer's position is moved in synchrony with the laser focal spot. Two-dimensional data acquisition is enabled by horizontal scanning of both light illumination and acoustic detection components along the axle of the blood vessel, and can certainly be extended three-dimensionally.

A nanosecond pulsed laser illuminates the engineered blood vessel at multiple wavelengths for spectrally resolving the three fluorescence probes. By combining the absorption coefficients and heat converting efficiency for different fluorescence probes at various wavelengths, multiple fluorescence probes can be differentiated simultaneously. At the same time, emitted fluorescent signals can be incorporated for even better FTM reconstruction.

Figure 15:
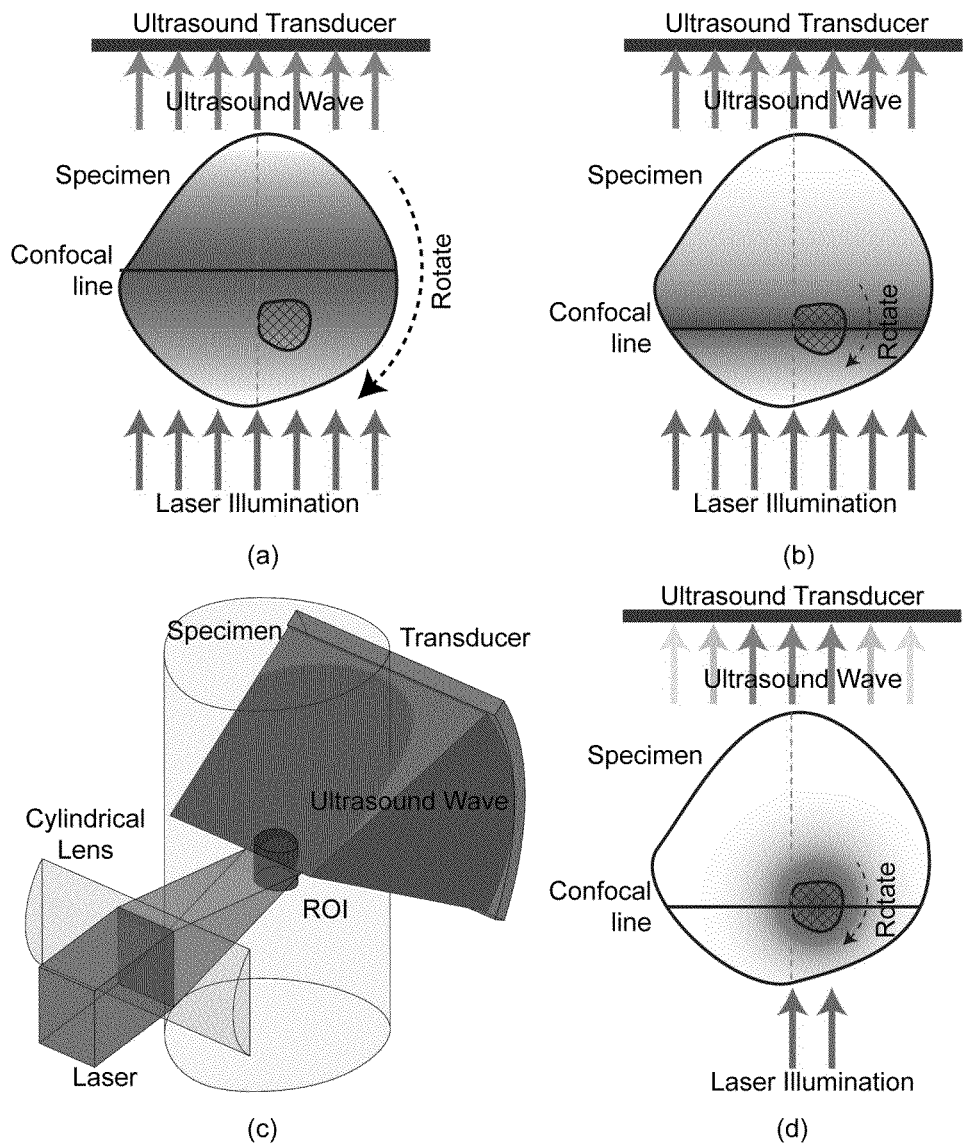
FIGS. 15A-B &D are interior photoacoustic tomography scans.
FIG. 15C is a three-dimensional schematic of photoacoustic tomography of an internal ROI with a focused laser beam in a specimen.

Interior PAT. The trans-illumination photoacoustic tomography design [104A] works in an x-ray CT style using a filtered back-projection algorithm. As shown in FIG. 15, the illumination laser and the cylindrical transducer are under a confocal setting. While the specimen is rotated by 360 degrees, the confocal line scans a section through the specimen. Based on the time-domain ultrasound signal, filtered back-projection algorithm can reconstruct the induced ultrasound source [104A]. If we are only interested in a small region of interests (ROI) in a specimen or an animal, it is possible to use interior tomography techniques [110A, 111A] for reconstruction of the ROI from truncated PAT data. To obtain the truncated PAT data for the ROI, we can configure the hardware and software of the PAT system to target the photoacoustic signal across the ROI. As shown in FIG. 15, because the PAT system has the highest sensitivity around the confocal line, we can adjust the position of the specimen to make the confocal line or zone cross or cover the ROI. The rotation of the specimen should be around the ROI to let the confocal zone scan the ROI during the rotation. Since the speed of light is several hundred times faster than sound in tissue, the heating can be considered as an instant process compared to the sound wave propagation. Hence, we can filter the time domain ultrasound signal to remove/reduce the signal that is not across the ROI. This truncated PAT data, can reduce reconstruction noise and improve image quality.

It is also possible to reduce the width of the scanning laser to focus the energy on the ROI. As shown in FIGS. 20 (c) and (d), the width of the illumination laser is reduced to just cover the ROI. This reduces the light energy outside the ROI and keep the same energy level in the ROI compared to a full-width scan. Hence, a local scan can reduce unwanted ultrasound signals. We can also increase the size of the cylindrical transducer and place it closer to the object to gain better signal to noise ratios for the ultrasound signal in the ROI.

Figure 16:
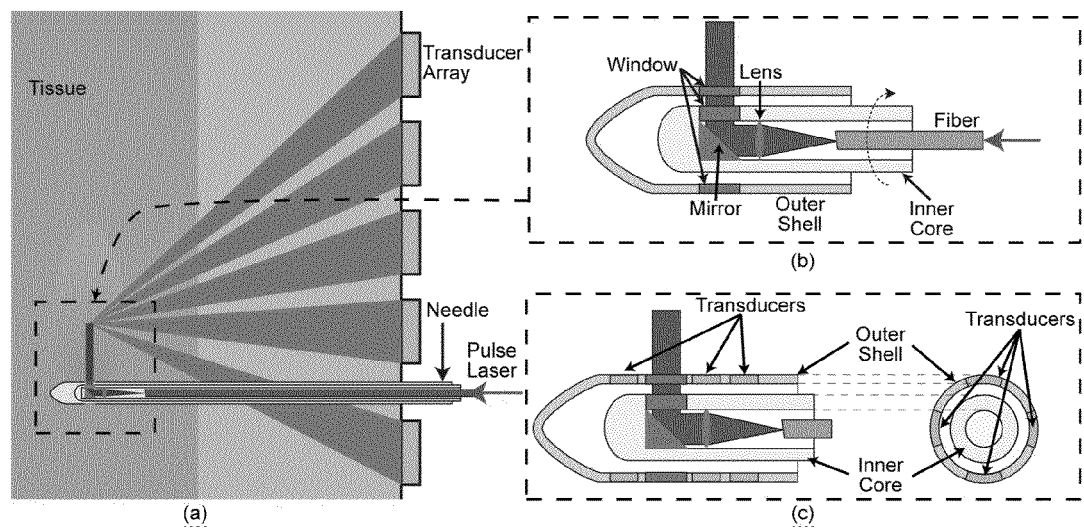
FIG. 16A is a schematic diagram showing the overall optical-biopsy-based photoacoustic tomography.

Optical Biopsy PAT. The depth of PAT is mainly restricted by the penetration of the illumination light. To gain a detectable ultrasound signal on the surface, strong enough light energy needs to be delivered into the tissue within a short pulse. The optical scattering and absorption limit the light energy penetration within several centimeters. On the other hand, optical biopsy can deliver an optical signal deeply by inserting an optical fiber into almost any ROI [112A-114A]. Optical biopsy can then induce photoacoustic waves in the same spirit as the traditional PAT. As shown in FIGS. 21 (a) and (b), an optic needle is moved into a target region. The needle has an outer shell and a needle core, which can be freely rotated within the outer shell to scan the focused laser. Hence, a helical or another style laser scan can be achieved while the needle is inserted in the tissue. A transducer array is attached on the tissue surface to pick up the induced ultrasound signal. Using a synthetic aperture image reconstruction algorithm [115A] or another appropriate algorithm, the photoacoustic image can be reconstructed. As shown in FIGS. 21 (a) and (b), the illumination laser is formed into a pencil beam. By adjusting the distance between the fiber tip and the lens (FIG. 14), the illumination laser can be beamed at different tissue depths. It is also possible to integrate the photon heating and ultrasound detection all in the same needle. The thickness of the ultrasound transducer is proportional to the inverse of the central wavelength of the transducer. The thickness of a high frequency ultrasound transducer could be less than half millimeter. Hence, we can embed several transducers on the outer shell of the biopsy needle, as shown in FIG. 16 (c). Multi-wavelength/multi-spectral imaging modes can also be similarly designed by utilizing a tunable laser.

The optical approach for molecular imaging offers significant advancements in regenerative medicine and tissue engineering research because of its specificity, sensitivity, ease-of-operation, and cost effectiveness. However, 2D-based optical molecular imaging techniques, especially those based on bioluminescence and fluorescence probes, may not be appropriate for some clinical applications due to difficulties in quantification of detailed tissue remodeling. On the other hand, recently emerging bioluminescence and fluorescence tomography allows 3D reconstruction and quantification of internal bioluminescently or fluorescently labeled cells in vivo [22A, 45A, 46A]. Therefore, optical molecular tomography can be developed as an enabling tool for a variety of regenerative-medicine and tissue-engineering applications. State-of-the-art optical-molecular and cellular-imaging techniques can be combined with functional analyses to elucidate tissue growth and maturation. This method is likely to lead to significant new discoveries and therapies that are clinically relevant and to circumvent some of the problems associated with current tissue-engineering and cellular-therapy approaches. Optical molecular tomography will address the challenges in regenerative medicine in an innovative and comprehensive manner. The hybrid optical system is a modality fusion of OCT, DOT, and FMT, which can utilize multiple fluorescence probes for imaging of multiple cell types and a scaffold, a molecular imaging system especially useful, for example, to evaluate the regeneration process under minimal disturbing and even in vivo scenarios.

REFERENCES

1A. Atala, A., Engineering tissues, organs and cells. Journal of Tissue Engineering and Regenerative Medicine, 2007. 1(2): p. 83-96.

2A. Contag, C. H. and M. H. Bachmann, Advances in vivo bioluminescence imaging of gene expression. Annual Review of Biomedical Engineering, 2002. 4: p. 235-260.

3A. Ntziachristos, V., et al., Looking and listening to light: the evolution of whole-body photonic imaging. Nature Biotechnology, 2005. 23(3): p. 313-320.

4A. Ray, P., A. M. Wu, and S. S. Gambhir, Optical bioluminescence and positron emission tomography imaging of a novel fusion reporter gene in tumor xenografts of living mice. Cancer Res., 2003. 63(6): p. 1160-1165.

5A. Rice, B. W., M. D. Cable, and M. B. Nelson, In vivo imaging of light-emitting probes. Journal of Biomedical Optics, 2001. 6(4): p. 432-440.

6A. Jaffer, F. A. and R. Weissleder, Molecular imaging in the clinical arena. Jama-Journal of the American Medical Association, 2005. 293(7): p. 855-862.

7A. Thakur, M. and B. C. Lentle, Report of a summit on molecular imaging. Radiology, 2006. 236(3): p. 753-755.

8A. Weissleder, R. and V. Ntziachristos, Shedding light onto live molecular targets. Nature Medicine, 2003. 9(1): p. 123-128.

9A. Choy, G., P. Choyke, and S. K. Libutti, Current advances in molecular imaging: Noninvasive in vivo bioluminescent and fluorescent optical imaging in cancer research. Molecular Imaging, 2003. 2(4): p. 303-312.

10A. Edinger, M., et al., Advancing animal models of neoplasia through in vivo bioluminescence imaging. European Journal Of Cancer, 2002. 38(16): p. 2128-2136.

11A. Kang, Y. B., et al., In vivo gene transfer using a nonprimate lentiviral vector pseudotyped with Ross River Virus glycoproteins. J. of Virology, 2002. 76(18): p. 9378-9388.

12A. Mandl, S., et al., Understanding immune cell trafficking patterns via in vivo bioluminescence imaging. Journal of Cellular Biochemistry, 2002: p. 239-248.

13A. McCaffrey, A., M. A. Kay, and C. H. Contag, Advancing molecular therapies through in vivo bioluminescent imaging. Molecular Imaging, 2003. 2(2): p. 75-86.

14A. Rehemtulla, A., et al., Rapid and quantitative assessment of cancer treatment response using in vivo bioluminescence imaging. Neoplasia, 2000. 2(6): p. 491-495.

15A. Söling, A. and N. G. Rainov, Bioluminescence imaging in vivo-application to cancer research. Expert Opinion on Biological Therapy 2003. 3(7): p. 1163-1172.

16A. Wu, J. C., et al., Molecular imaging of cardiac cell transplantation in living animals using optical bioluminescence and positron emission tomography. Circulation, 2003. 108(11): p. 1302-1305.

17A. Zabner, J., et al., Adeno-associated virus type 5 (AAV5) but not AAV2 binds to the apical surfaces of airway epithelia and facilitates gene transfer. Journal of Virology, 2000. 74(8): p. 3852-3858.

18A. Helmchen, F. and W. Denk, Deep tissue two-photon microscopy. Nat Methods, 2005. 2(12): p. 932-40.

19A. So, M. K., et al., Self-illuminating quantum dot conjugates for in vivo imaging. Nature Biotechnology, 2006. 24(3): p. 339-343.

20A. Wang, G., E. A. Hoffman, and G. McLennan, Systems and methods for bioluminescent computed tomographic reconstruction. 2002, US Patent Office: US.

21A. Joshi, A. and E. M. Sevick-Muraca, Adaptive finite element methods for distributed parameter system identification: Applications in fluorescence enhanced frequency domain optical tomography. Proceedings of the 2004 American Control Conference, Vols 1-6, 2004: p. 2263-2267.

22A. Wang, G., et al., In vivo mouse studies with bioluminescence tomography. Optics Express, 2006. 14(17): p. 7801-7809.

23A. Vinegoni, C., et al., In vivo imaging of Drosophila melanogaster pupae with mesoscopic fluorescence tomography. Nature Methods, 2008. 5(1): p. 45-47.

24A. Wang, G., E. A. Hoffman, and G. McLennan, Systems and methods for bioluminescent computed tomographic reconstruction. 2004: US.

25A. Wang, G., Y. Li, and M. Jiang, Uniqueness theorems in bioluminescence tomography. Medical Physics, 2004. 31(8): p. 2289-2299.

26A. Busbridge, I. W., The mathematics of radiative transfer. 1960, Cambridge [Eng.]: University Press. 143 p.

27A. Case, K. M. and P. F. Zweifel, Linear transport theory. Addison-Wesley series in nuclear engineering. 1967, Reading, Mass.: Addison-Wesley Pub. Co. ix, 342 p.

28A. Chandrasekhar, S., Rad. transf. 1950, Oxford: Clarendon Press. xiv, 393 p.

29A. Kim, A. D., Transport theory for light propagation in biological tissue. J Opt Soc Am A Opt Image Sci Vis, 2004. 21(5): p. 820-7.

30A. Klose, A. D., V. Ntziachristos, and A. H. Hielscher, The inverse source problem based on the radiative transfer equation in optical molecular imaging. Journal of Computational Physics, 2005. 202(1): p. 323-345.

31A. Prahl, S., Light transport in tissue. 1988, University of Texas at Austin.

32A. Flock, S. T., et al., Monte-Carlo Modeling of Light-Propagation in Highly Scattering Tissues.1. Model Predictions and Comparison with Diffusion-Theory. Ieee Transactions on Biomedical Engineering, 1989. 36(12): p. 1162-1168.

33A. Flock, S. T., B. C. Wilson, and M. S. Patterson, Monte-Carlo Modeling of Light-Propagation in Highly Scattering Tissues.2. Comparison with Measurements in Phantoms. IEEE Transactions on Biomedical Engineering, 1989. 36(12): p. 1169-1173.

34A. Keijzer, M., et al., Light distributions in artery tissue: Monte Carlo simulations for finite-diameter laser beams. Lasers Surg Med, 1989. 9(2): p. 148-54.

35A. Li, H., et al., A mouse optical simulation environment (MOSE) to investigate bioluminescent phenomena in the living mouse with the Monte Carlo method. Acad Radiol, 2004. 11(9): p. 1029-38.

36A. Manno, I., Introduction to the Monte-Carlo method. 1999, Budapest: Akadémiai Kiadó. 162 p.

37A. Wang, L., S. L. Jacques, and L. Zheng, MCML—Monte Carlo modeling of light transport in multi-layered tissues. Comp. Methods Progr. Biomed, 1995. 47(2): p. 131-46.

38A. Wilson, B. C. and G. Adam, A Monte Carlo model for the absorption and flux distributions of light in tissue. Med Phys, 1983. 10(6): p. 824-30.

39A. Arridge, S., Optical tomography in medical imaging. Inverse Problems, 1999. 15: p. R41-R93.

40A. Klose, A. D. and E. W. Larsen, Light transport in biological tissue based on the simplified spherical harmonics equations. J. of Computational Phy., 2006. 220: p. 441-470.

41A. Cong, W., et al., Flux vector formulation for photon propagation in the biological tissue. Optics Letters, 2007. 32(19): p. 2837-2839.

42A. Cong, W., et al., Modeling photon propagation in biological tissues using a generalized Delta-Eddington phase function. Physical Review E, 2007. 76(5): p. 051913.

43A. Cong, W., et al., Integral equations of the photon fluence rate and flux based on a generalized Delta-Eddington phase function. J. of Biomed. Opt., 2008. 13: p. 024016.

44A. Cheong, W. F., S. A. Prahl, and A. J. Welch, A review of the optical properties of biological tissues. IEEE J. Quantum Electron., 1990. 26: p. 2166-2185.

45A. Massoud, T. F. and S. S. Gambhir, Molecular imaging in living subjects: seeing fundamental biological processes in a new light. Genes & Dev., 2003. 17(5): p. 545-580.

46A. Sevick-Muraca, E. M. and J. C. Rasmussen, Molecular imaging with optics: primer and case for near-infrared fluorescence techniques in personalized medicine. Journal of Biomedical Optics, 2008. 13(4): p.-.

47A. Cong, A., et al., Optical Property Characterization Based on a Phase Approximation Model. 2009.

48A. Huang, D., et al., Optical Coherence Tomography. Science, 1991. 254(5035): p. 1178-1181.

49A. Rylander, C. G., T. E. Milner, and J. S. Nelson, Mechanical tissue optical clearing devices: Enhancement of light penetration and heating of ex-vivo porcine skin and adipose tissue. Lasers in Surgery and Medicine, 2008: p. 20-20.

50A. Rylander, C. G., et al., Dehydration mechanism of optical clearing in tissue. Journal of Biomedical Optics, 2006. 11(4): p.-.

51A. Bonnema, G. T., et al., Assessment of blood vessel mimics with optical coherence tomography. Journal of Biomedical Optics, 2007. 12(2): p.-.

52A. Bonnema, G. T., et al., An automatic algorithm for detecting stent endothelialization from volumetric optical coherence tomography datasets. Physics in Medicine and Biology, 2008. 53(12): p. 3083-3098.

53A. de Boer, J. F., et al., Improved signal-to-noise ratio in spectral-domain compared with time-domain optical coherence tomography. Opt Lett, 2003. 28(21): p. 2067-69.

54A. Fercher, A. F., et al., Measurement of Intraocular Distances by Backscattering Spectral Interferometry. Optics Communications, 1995. 117(1-2): p. 43-48.

55A. Choma, M. A., C. H. Yang, and J. A. Izatt, Instantaneous quadrature low-coherence interferometry with 3×3 fiber-optic couplers. Opt. Lett., 2003. 28(22): p. 2162-2164.

56A. Huber, R., M. Wojtkowski, and J. G. Fujimoto, Fourier Domain Mode Locking (FDML): A new laser operating regime and applications for optical coherence tomography. Optics Express, 2006. 14(8): p. 3225-3237.

57A. Biedermann, B. R., et al., Real time en face Fourier-domain optical coherence tomography with direct hardware frequency demodulation. Optics Letters, 2008. 33(21): p. 2556-2558.

58A. Pickering, J. W., et al., Double-Integrating-Sphere System for Measuring the Optical-Properties of Tissue. Applied Optics, 1993. 32(4): p. 399-410.

59A. Prahl, S. A., M. J. C. Vangemert, and A. J. Welch, Determining the Optical-Properties of Turbid Media by Using the Adding-Doubling Method. Applied Optics, 1993. 32(4): p. 559-568.

60A. Hayakawa, C. K., et al., Perturbation Monte Carlo methods to solve inverse photon migration problems in heterogeneous tissues. Optics Letters, 2001. 26(17): p. 1335-1337.

61A. Hielscher, A. H., A. D. Klose, and K. M. Hanson, Gradient-based iterative image reconstruction scheme for time-resolved optical tomography. Ieee Transactions on Medical Imaging, 1999. 18(3): p. 262-271.

62A. Wang, G., et al., Development of the first bioluminescent CT scanner. Radiology, 2003. 229: p. 566.

63A. Kuo, C., et al., Three-dimensional reconstruction of in vivo bioluminescent sources based on multispectral imaging. Journal of Biomedical Optics, 2007. 12(2): p.-.

64A. Gu, X. J., et al., Three-dimensional bioluminescence tomography with model-based reconstruction. Optics Express, 2004. 12(17): p. 3996-4000.

65A. Chaudhari, A. J., et al., Hyperspectral and multispectral bioluminescence optical tomography for small animal imaging. Phys. Med. Biol., 2005. 50: p. 5421-5441.

66A. Cong, W. X., et al., Practical reconstruction method for bioluminescence tomography. Optics Express, 2005. 13(18): p. 6756-6771.

67A. Comsa, D. C., T. J. Farrell, and M. S. Patterson, Quantification of bioluminescence images of point source objects using diffusion theory models. Phys Med Biol, 2006. 51(15): p. 3733-46.

68A. Han, W. M., W. X. Cong, and G. Wang, Mathematical theory and numerical analysis of bioluminescence tomography. Inverse Problems, 2006. 22(5): p. 1659-1675.

69A. Cong, A. and G. Wang, Multi-spectral bioluminescence tomography: Methodology and simulation. Int'l J. of Biomed. Imaging, 2006. ID57614: p. 1-7.

70A. Dehghani, H., et al., Spectrally resolved bioluminescence optical tomography. Optics Letters, 2006. 31(3): p. 365-367.

71A. Han, W. M., W. X. Cong, and G. Wang, Mathematical study and numerical simulation of multispectral bioluminescence tomography. International Journal of Biomedical Imaging, 2006. Article ID 54390: p. 10.

72A. Wang, G., H. Shen, and K. Durairaj, The First Bioluminescence Tomography System for Simultaneous Acquisition of Multiview and Multispectral Data. International Journal of Biomedical Imaging, 2006. Vol. 2006: p. Article ID 58601, Pages 1-8.

73A. Wang, G., et al., Digital spectral separation methods and systems for bioluminescence imaging. Optics Express, 2008. 16(3): p. 1719-1732.

74A. Klose, A. D., Transport-theory-based stochastic image reconstruction of bioluminescent sources. Journal of the Optical Society of America a-Optics Image Science and Vision, 2007. 24(6): p. 1601-1608.

75A. Wang, G., et al., Multi-spectral bioluminescence tomography methods and systems. 2004, Patent disclosure filed with Univ. of Iowa Research Foundation in April.

76A. Wang, G., et al., Temperature-modulated bioluminescence tomography. Optics Express, 2006. 14(17): p. 7852-7871.

77A. Zacharakis, G., et al., Volumetric tomography of fluorescent proteins through small animals in vivo. Proceedings of the National Academy of Sciences of the United States of America, 2005. 102(51): p. 18252-18257.

78A. Zacharakis, G. and J. Ripoll, Fluorescent protein tomography scanner for small animal imaging. IEEE Transactions On Medical Imaging, 2005. 24(7): p. 878-885.

79A. Qian, X. M., et al., In vivo tumor targeting and spectroscopic detection with surface-enhanced Raman nanoparticle tags. Nature Biotechnology, 2008. 26(1): p. 83-90.

80A. Roy, R., A. Godavarty, and E. M. Sevick-Muraca, Fluorescence-enhanced three-dimensional lifetime imaging: a phantom study. Physics in Medicine and Biology, 2007. 52(14): p. 4155-4170.

81A. Joshi, A., et al., Multi-modality CT-PET-NIR fluorescence tomography. 2008 IEEE Inter. Symp. on Biomed. Imag.: From Nano to Macro, Vols 1-4, 2008: p. 1601-04.

82A. Joshi, A., et al., Radiative transport-based frequency-domain fluorescence tomography. Physics in Medicine and Biology, 2008. 53(8): p. 2069-2088.

83A. Lee, J. H., A. Joshi, and E. M. Sevick-Muraca, Fully adaptive finite element based tomography using tetrahedral dual-meshing for fluorescence enhanced optical imaging in tissue. Optics Express, 2007. 15(11): p. 6955-6975.

84A. Turchin, I. V., et al., Fluorescence diffuse tomography for detection of RFP-expressed tumors in small animals. Molecular Imaging, 2007. 6626: p. U104-U111.

85A. Deliolanis, N., et al., In-vivo lung cancer imaging in mice using 360 degrees free-space fluorescence molecular tomography. 2006 28th Annual International Conference of the IEEE Engineering in Med. and Bio. Society, Vols 1-15, 2006: p. 2828-30.

86A. Tsien, R. Y., Building and breeding molecules to spy on cells and tumors. FEBS Letters, 2005. 579(4): p. 927-932.

87A. Achilefu, S. and S. Bloch. Synergistic effects of light-emitting probes and peptides for targeting and monitoring integrin expression. in Proc. Natl. Acad. Sci. USA. 2005.

88A. Tung, C. H., Fluorescent peptide probes for in vivo diagnostic imaging. Biopolymers—Peptide Science Section, 2004. 76(5): p. 391-403.

89A. Weissleder, R., et al., In vivo imaging of tumors with protease-activated near-infrared fluorescent probes. Nat. Biotechnol., 1999. 17: p. 375-378.

90A. Ntziachristos, V., Fluorescence molecular imaging Annual Review of Biomedical Engineering, 2006. 8: p. 1-33.

91A. Lee, S. J., et al., Development of a composite vascular scaffolding system that withstands physiological vascular conditions. Biomaterials, 2008. 29(19): p. 2891-8.

92A. Lee, S. J., et al., In vitro evaluation of electrospun nanofiber scaffolds for vascular graft application. J Biomed Mater Res A, 2007. 83(4): p. 999-1008.

93A. Stitzel, J., et al., Controlled fabrication of a biological vascular substitute. Biomaterials, 2006. 27(7): p. 1088-94.

94A. Lee, S. J., et al., The use of thermal treatments to enhance the mechanical properties of electrospun poly(epsilon-caprolactone) scaffolds. Biom., 2008. 29(10): p. 1422-30.

95A. Gavenis, K., et al., Optical Coherence Tomography (OCT) to Evaluate Cartilage Tissue Engineering. Zeitschrift Fur Ortho. Und Unfall., 2008. 146(6): p. 788-792.

96A. Yang, Y., et al., Characterisation of scaffold architecture and tendons using optical coherence tomography and polarisation-sensitive optical coherence tomography. Iet Optoelectronics, 2008. 2(5): p. 188-194.

97A. Eder, K., R. Schmitt, and R. Muller-Rath, Imaging of artificial cartilage with optical coherence tomography—art. no. 68580J. Optics in Tissue Engineering and Regenerative Medicine Ii, 2008. 6858: p. J8580-J8580.

98A. Bagnaninchi, P. O., A. El Haj, and Y. Yang, Continuous monitoring of tissue growth inside a perfusion bioreactor by optical coherence tomography—art. no. 643903. Optics in Tissue Engineering and Regenerative Medicine, 2007. 6439: p. 43903-43903.

99A. Spoler, F., et al., High-resolution optical coherence tomography as a non-destructive monitoring tool for the engineering of skin equivalents Skin Research and Technology, 2006. 12(4): p. 261-267.

100A. Mason, C., et al., The potential of optical coherence tomography in the engineering of living tissue. Physics in Medicine and Biology, 2004. 49(7): p. 1097-1115.

101A. Diebold, G. J., T. Sun, and M. I. Khan, Photoacoustic Monopole Radiation in 1-Dimension, 2-Dimension, and 3-Dimension. Physical Rev. Lett., 1991. 67(24): p. 3384-87.

102A. Park, S. M., et al., Photoacoustic Effect in Strongly Absorbing Fluids. Ultrasonics, 1991. 29(1): p. 63-67.

103A. De La Zerda, A., et al., Carbon nanotubes as photoacoustic molecular imaging agents in living mice. Nature Nanotechnology, 2008. 3(9): p. 557-562.

104A. Ermilov, S. A., et al. Development of laser optoacoustic and ultrasonic imaging system for breast cancer utilizing handheld array probes. in Photons Plus Ultrasound: Imaging and Sensing 2009 2009. San Jose, Calif., USA: SPIE.

105A. Maslov, K., G. Stoica, and L. H. V. Wang, In vivo dark-field reflection-mode photoacoustic microscopy. Optics Letters, 2005. 30(6): p. 625-627.

106A. Razansky, D., et al., Multispectral opto-acoustic tomography of deep-seated fluorescent proteins in vivo. Nature Photonics, 2009. 3: p. 412-417.

107A. Wang, X. D., et al., Noninvasive laser-induced photoacoustic tomography for structural and functional in vivo imaging of the brain. Nat. Biotech., 2003. 21(7): p. 803-06.

108A. Xu, M. H., G. Ku, and L. H. V. Wang, Microwave-induced thermoacoustic tomography using multi-sector scanning Medical Physics, 2001. 28(9): p. 1958-1963.

109A. Xu, M. H. and L. H. V. Wang, Universal back-projection algorithm for photoacoustic computed tomography. Physical Review E, 2005. 71(1): p.-.

110A. Wang, G., H. Yu, and Y. Ye, A scheme for multi-source interior tomography. Med. Phys., 2009. 36(8): p. 3575-3581.

111A. Ye, Y., H. Yu, and G. Wang, Exact interior reconstruction with cone-beam CT. Internation Journal of Biomedical Imaging, 2008. 2008: p. Article ID 10693.

112A. Cong, A. X., et al., Compressive-sensing-based computational optical biopsy. 2009.

113A. Li, Y., M. Jiang, and G. Wang, Computational optical biopsy. Biomed Eng Online, 2005. 4(1): p. 36.

114A. Shen, H. O., et al., Numerical study on the validity of the diffusion approximation for computational optical biopsy. Journal of the Optical Society of America a-Optics Image Science and Vision, 2007. 24(2): p. 423-429.

115A. Wang, L. V. and H.-i. Wu, Biomedical optics: principles and imaging. 2007, Hoboken, N. J.: Wiley-Interscience. xiv, 362 p.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. It is intended that the specification and examples be considered as exemplary in nature and that variations that do not depart from the essence of the invention are intended to be within the scope of the invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. The indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

Throughout this application, various publications are referenced. The disclosures of these publications in their entireties are hereby incorporated by reference into this application in order to more fully describe the features of the invention and/or the state of the art to which this pertains. The references disclosed are also individually and specifically incorporated by reference herein for the material contained in them that is discussed in the portion of this disclosure in which the reference is relied upon.

The invention claimed is:

1. A computed tomography based imaging system comprising:
    at least one wide-beam gray-scale imaging chain capable of performing a global scan of an object and acquiring projection data relating to the object;
    at least one narrow-beam true-color imaging chain capable of performing a spectral interior scan of a region of interest (ROI) of and acquiring projection data relating to the object;
    a processing module operably configured for:
        receiving the projection data;
        reconstructing the ROI into an image by analyzing the data with a color interior tomography algorithm, aided by an individualized gray-scale reconstruction of an entire field of view (FOV), including the ROI; and
    a processor for executing the processing module.

2. The system of claim 1, wherein each imaging chain comprises an x-ray source and detector pair, and each pair is operably disposed on a common rotating slip ring.

3. The system of claim 1, further comprising multi-source interior true-color micro-CT for ultra-fast data acquisition.

4. The system of claim 1, wherein the imaging chains are operated simultaneously or sequentially or combination thereof.

5. The system of claim 1, wherein the interior tomography algorithm is further operably configured for:
    reconstructing the local images using the datasets from different energy levels;
    extracting features from reconstructed images of different energy levels.

6. The system of claim 5, wherein the processing module is operably configured for extracting features for volume information using the principal component analysis method.

7. A computed tomography based imaging method comprising:
    performing a global scan of an object and acquiring projection data relating to the object using at least one wide-beam gray-scale imaging chain;
    performing a spectral interior scan of a region of interest (ROI) of and acquiring projection data relating to the object using at least one narrow-beam true-color imaging chain;
    reconstructing the ROI into an image by analyzing the projection data with a color interior tomography algorithm, aided by an individualized gray-scale reconstruction of an entire field of view (FOV), including the ROI.

8. The method of claim 7, wherein each imaging chain comprises an x-ray source and detector pair, and each pair is operably disposed on a common rotating slip ring.

9. The method of claim 8, further comprising multi-source interior true-color micro-CT for ultra-fast data acquisition.

10. The method of claim 8, wherein the imaging chains are operated simultaneously or sequentially or a combination thereof.

11. The method of claim 8, wherein the interior tomography algorithm is further operably configured for:
    reconstructing the local images using the datasets from different energy levels;
    extracting features from all the reconstructed images of different energy levels.

12. The method of claim 11, wherein the principal component analysis method is used to extract features for volume information.

* * * * *

UNITED STATES PATENT AND TRADEMARK OFFICE
CERTIFICATE OF CORRECTION

PATENT NO. : 8,862,206 B2  
APPLICATION NO. : 12/945733  
DATED : October 14, 2014  
INVENTOR(S) : Wang et al.

Page 1 of 1

It is certified that error appears in the above-identified patent and that said Letters Patent is hereby corrected as shown below:

In the Specification

Column 1, Lines 17 to 21 are corrected as follows:

Delete current paragraph:
"This work was partially supported by the National Institutes of Health under NIH Grants EB001685, CA127189, CA135151, EB002667, EB004287, EB007288, and HL098912. The U.S. Government has certain rights in this invention."

Insert corrected paragraph:
--This invention was made with government support under Grant Nos. CA127189 and EB001685 awarded by the National Institutes of Health. The Government has certain rights in the invention.--

Signed and Sealed this
Fifteenth Day of September, 2015

Michelle K. Lee
*Director of the United States Patent and Trademark Office*